United States Patent [19]
Ostresh et al.

[11] Patent Number: 5,856,107
[45] Date of Patent: Jan. 5, 1999

[54] COMBINATORIAL LIBRARIES OF IMIDAZOL-PYRIDO-INDOLE AND IMIDAZOL-PYRIDO-BENZOTHIOPHENE DERIVATIVES, METHODS OF MAKING THE LIBRARIES AND COMPOUNDS THEREIN

[75] Inventors: John M. Ostresh, Encinitas; Richard A. Houghten, Del Mar, both of Calif.

[73] Assignee: Trega Biosciences, Inc., San Diego, Calif.

[21] Appl. No.: 794,364

[22] Filed: Feb. 4, 1997

[51] Int. Cl.$^6$ .................. G01N 33/53; C07D 491/00; C07D 513/00
[52] U.S. Cl. .................. 435/7.1; 436/501; 436/518; 546/64
[58] Field of Search .................. 435/7.1; 436/501, 436/91, 518; 546/64

[56] References Cited

FOREIGN PATENT DOCUMENTS 46-027196  8/1971  Japan .

OTHER PUBLICATIONS

Gordon EM, et al, (1994) Applications of combinatorial technologies to drug discovery. 2. Combinatorial organic synthesis, library screening strategies, and future directions. J. Med. Chem. 37: 1385–1401, 1994.
Mayer et al., "Application Of the Pictet–Spengler Reaction In Combinatorial Chemistry." *Tetrahedron Letters*, 37(32):5633–5636 (1996).
Kaljuste and Unden, "Solid Phase Synthesis of 1,2,3, 4–Tetrahydro–β–carbolines; Implications for Combinatorial Chemistry." *Tetrahedron Letters*, 36(50):9211–9214 (1995).
Yang and Guo, "Pictet–Spengler Reaction On Solid Support." *Tetrahedron Letters*, 37(29):5041–5044 (1996).
Kanaoka et al., "Amino Acids and Peptides–II$^1$. Cyclodehydration of Some Tryptophan–Dipeptides and Their Derivatives with Polyphosphate Ester." *Tetrahedron*, 24:2591–2594 (1968).
Ostresh et al., "Peptide Libraries: Determination of Relative Reaction Rates of Protected Amino Acids in Competitive Couplings." *Biopolymers.*, 84:1661–1689 (1994).
Gordon et al., "Applications of combinatorial technologies to drug discovery. 2. Combinatorial organic synthesis, library screening strategies, and future directions." *J. of Med. Chem.*, 37(10):1386–1401 (1994).
Gallop et al., "Applications of combinatorial technologies to drug discovery. 1. Background and peptide combinatorial libraries." *J. of Med. Chem.*, 37(9):1233–1251 (1994).
Ostresh et al., "Libraries from libraries: Chemical transformation of combinatorial libraries to extend the range and repertoire of chemical diversity." *Proc. Natl., Acad. Sci. USA*, 9:11138–11142 (1994).
Pinilla et al., "Rapid Identification of High Affinity Peptide Ligands Using Positional Scanning Synthetic Peptide Combinatorial Libraries." *BioTecniques*, 13(6):901–905 (1992).
Houghten et al., "Generation and use of synthetic peptide combinatorial libraries for basic research and drug discovery." *Nature*, 354:84–86 (1991).

*Primary Examiner*—Lora M. Green
*Attorney, Agent, or Firm*—Campbell & Flores LLP

[57] ABSTRACT

The invention provides a rapid approach for combinatorial synthesis and screening of libraries of imidazol-pyrido-indole and imidazol-pyrido-benzothiophene compounds. The present invention further provides methods of preparing the libraries and the individual compounds made by the combinatorial synthesis.

14 Claims, 2 Drawing Sheets

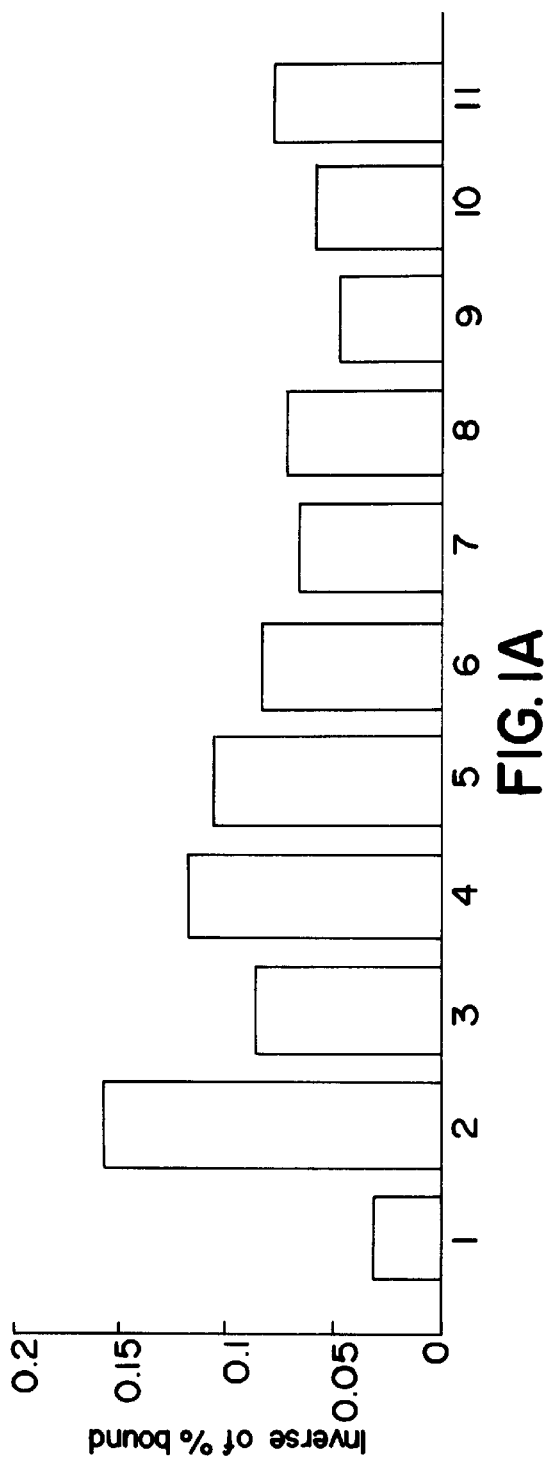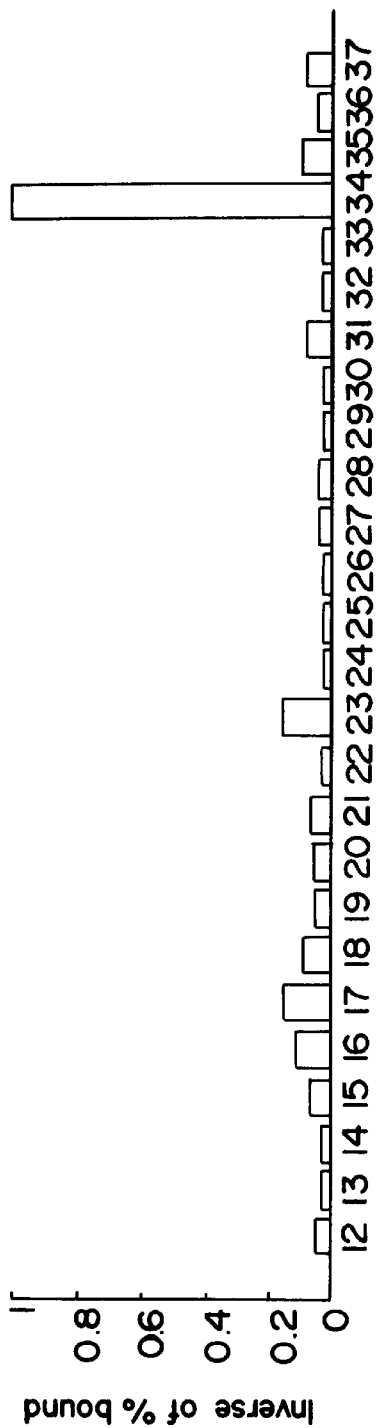

COMBINATORIAL LIBRARIES OF IMIDAZOL-PYRIDO-INDOLE AND IMIDAZOL-PYRIDO-BENZOTHIOPHENE DERIVATIVES, METHODS OF MAKING THE LIBRARIES AND COMPOUNDS THEREIN

BACKGROUND OF THE INVENTION

1. Field of the Invention

The present invention relates generally to the combinatorial synthesis of imidazol-pyrido-indole and imidazol-pyrido-benzothiophene derivatives. More specifically, the invention provides novel imidazol-pyrido-indole and imidazol-pyrido-benzothiophene derivatives as well as novel combinatorial libraries comprised of many such compounds, and methods of synthesizing the libraries.

2. Background Information

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as the imidazol-pyrido-indole and imidazol-pyrido-benzothiophene compounds of the present invention.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, in U.S. Pat. Nos. 5,367,053 by Dooley, and 5,182,366 by Huebner, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such libraries and the rapid screening of the library which identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide libraries has led to the identification of many biologically-active lead compounds. However, the therapeutic application of peptides is limited by their poor stability and bioavailability in vivo. Therefore, there is a need to synthesize and screen compounds which can maintain high affinity and specificity toward biological receptors but which have improved pharmacological properties relative to peptides.

Combinatorial approaches have recently been extended to "organic," or non-peptide, libraries. The organic libraries to the present, however, are of limited diversity and generally relate to peptidomimetic compounds; in other words, organic molecules that retain peptide chain pharmacophore groups similar to those present in the corresponding peptide. Although the present invention is principally derived from the synthesis of dipeptides, the dipeptides are substantially modified. In short, they are chemically modified through acylation and cyclization into the subject imidazol-pyrido-indoles and imidazol-pyrido-benzothiophenes, thus providing mixtures and individual compounds of substantial diversity.

The classical organic synthesis of variously substituted imidazol-pyrido-indoles is known. For example, as described in Konaoka et al., *Tetrahedron,* 24:2591 (1968), imidazol-pyrido-indoles can be obtained from the Bischler-Napieralski cyclization of tryptophan-containing derivatives. However, the current synthesis and study of imidazol-pyrido-indoles is a slow process. Each imidazole must be individually synthesized and separately tested. There exists a need to more efficiently synthesize and test various imidazol-pyrido-indole of substantial diversity.

Combinatorial technology has been used for the solid-phase synthesis of relatively small libraries of β-carbolines. Such synthesis involves the condensation of a polymer bound tryptophan and an aldehyde or ketone component as described, for example, in Mayer et al., *Tet. Lett.,* 37:5633 (1996), Yang and Guo, *Tet. Lett.,* 37:5041 (1996) and Kaljuste and Unde'n, *Tet. Lett.,* 36:9211 (1995). However, there remains a need to apply combinatorial technology to more complex molecules such as imidazol-pyrido-indoles, and to libraries of greater diversity.

This invention satisfies these needs and provides related advantages as well. The present invention overcomes the known limitations to classical organic synthesis of imidazol-pyrido-indoles as well as the shortcomings of combinatorial chemistry with small organics or peptidomimetics. Moreover, the present invention provides a large array of diverse imidazol-pyrido-indole which can be screened for biological activity, and as described below, are biologically active.

SUMMARY OF THE INVENTION

The invention provides a rapid approach for combinatorial synthesis and screening of libraries of imidazol-pyrido-indole and imidazol-pyrido-benzothiophene compounds. The present invention further provides the compounds made by the combinatorial synthesis. More specifically, the present invention relates to the generation of synthetic combinatorial libraries of organic compounds based on the formula:

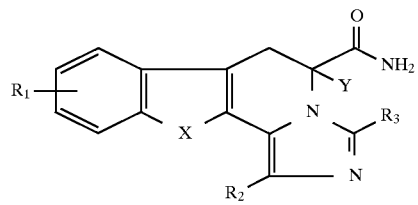

wherein $R^1$, $R^2$, $R^3$, X and Y have the meanings provided below.

BRIEF DESCRIPTION OF THE DRAWINGS

FIGS. 1(*a*) and 1(*b*) graphically show the results of the μ-opioid receptor assay of the subject library provided in Example III. Specifically, FIG. 1*a* graphically depicts the μ-opioid receptor assay data for combinatorial library pools 1 to 11, having the $R^1$ position constant and $R^2$ and $R^3$ variable in each of the eleven pools. FIG. 1*b* provides the data for combinatorial library pools 12 to 37, varying at the $R^1$ and $R^3$ positions and having $R^2$ constant.

DETAILED DESCRIPTION OF THE INVENTION

Figure 2:
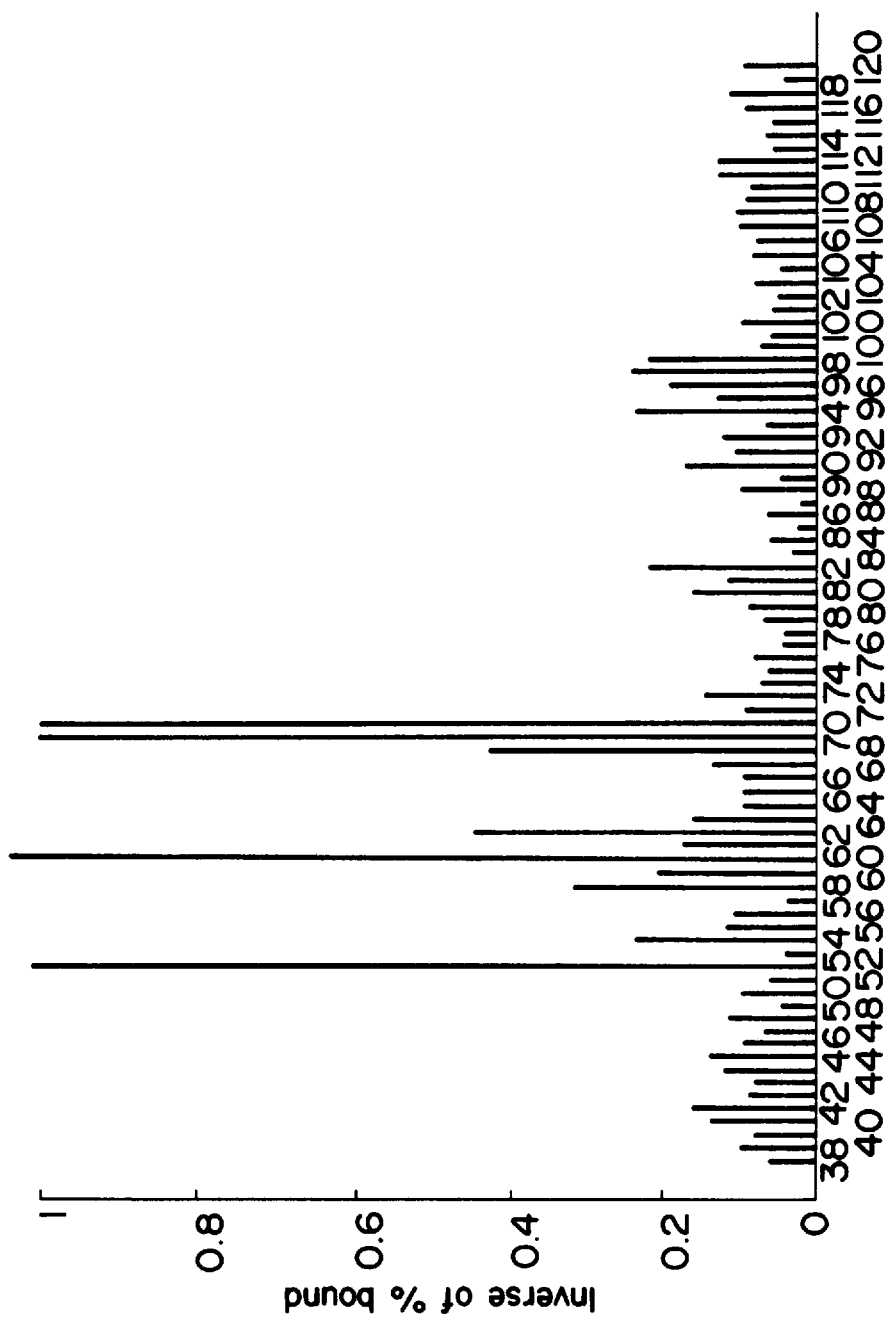
FIG. 2 graphically represents the results of the μ-opioid receptor assay screen for combinatorial library pools 38 to 121, with $R^1$ and $R^2$ variable while $R^3$ is constant in each of the pools.

The present invention relates to the generation of synthetic combinatorial libraries and individual compounds which are based on the Formula I:

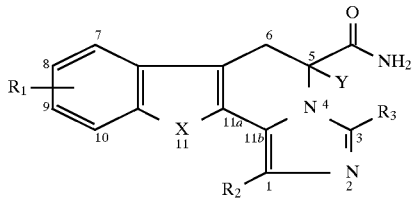

FORMULA I

Libraries and compounds contained therein having the structure of Formula I are imidazol-pyrido-indoles (X=N) and imidazol-pyrido-benzothiophenes (X=S), collectively referred to herein as "imidazoles". In the above Formula I:

$R^1$ is a hydrogen atom, halo, hydroxy, protected hydroxy, $C_1$ to $C_{10}$ alkyl, $C_1$ to $C_{10}$ substituted alkyl, amino, carboxy or protected carboxy;

$R^2$ is a hydrogen atom, $C_1$ to $C_{10}$ alkyl, $C_1$ to $C_{10}$ substituted alkyl, phenyl, substituted phenyl, $C_7$ to $C_{16}$ phenylalkyl, $C_7$ to $C_{16}$ substituted phenylalkyl, $C_3$ to $C_7$ cycloalkyl, $C_3$ to $C_7$ substituted cycloalkyl, benzyl, substituted benzyl, naphthyl, substituted naphthyl, or when taken in conjunction with C1 and N2 to form a piperidine or benzopiperidine;

$R^3$ is $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, $C_7$ to $C_{16}$ phenylalkenyl, $C_7$ to $C_{16}$ substituted phenylalkenyl, benzyl, substituted benzyl, naphthyl, substituted naphthyl, heterocycle, or substituted heterocycle;

X is a nitrogen atom (N) or a sulfur atom (S);

and Y is a hydrogen atom or methyl.

In one embodiment of the above imidazol-pyrido-indole and imidazol-pyrido-benzothiophene libraries and compounds, the substituents are as follows:

$R^1$ is a hydrogen atom, halo, hydroxy, or $C_1$ to $C_{10}$ alkyl;

$R^2$ is a hydrogen atom, $C_1$ to $C_{10}$ alkyl, $C_1$ to $C_{10}$ substituted alkyl, phenyl, $C_3$ to $C_7$ substituted cycloalkyl, benzyl, substituted benzyl, substituted naphthyl, or when taken in conjunction with C1 and N2 to form a piperidine or benzopiperidine;

$R^3$ is $C_1$ to $C_{10}$ alkyl, $C_1$ to $C_{10}$ substituted alkyl, $C_2$ to $C_{10}$ alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, $C_7$ to $C_{16}$ phenylalkenyl, $C_7$ to $C_{16}$ substituted phenylalkenyl, or heterocycle;

X is a nitrogen atom or a sulfur atom; and

Y is a hydrogen atom or methyl.

In yet another embodiment of the present invention, the libraries and compounds have the following substituents:

$R^1$ is a hydrogen atom, fluoro, bromo, hydroxy, or methyl, and, more preferably, a hydrogen atom, 9-fluoro, 8-fluoro, 8-bromo, 8-hydroxy, 11-methyl, 8-methyl, 9-methyl or 10-methyl;

$R^2$ is methyl, benzyl, a hydrogen atom, 3-imidazoylmethyl, aminobutyl, methylsulfinylethyl, carbamoylethyl, 4-hydroxybenzyl, ethyl, propyl, butyl, aminopropyl, phenyl, naphthylmethyl, cyclohexylmethyl, methylsulfonylethyl, 4-nitrobenzyl, 4-chlorobenzyl, 4-fluorobenzyl, 3-pyridylmethyl, 2-thienylmethyl, 1-butyl, 4-ethoxybenzyl, or when taken in conjunction with C1 and N2 to form a piperidine or benzopiperidine;

$R^3$ is 1-phenylcyclopropyl, 1-phenylproply, 2-phenylpropyl, 3-methylbenzyl, 3-fluorobenzyl, 3-bromobenzyl, 3-trifluoromethylbenzyl, 4-methylbenzyl, 4-fluorobenzyl, 3-methoxybenzyl, 4-bromobenzyl, 4-methoxybenzyl, 4-ethoxybenzyl, 4-isobutylphenethyl, 3,4-dichlorobenzyl, 3,5-bis(trifluoromethyl)-benzyl, 3,4-dimethoxyphenethyl, 4-phenylbenzyl, α-methylstyryl, 2-trifluoromethylstyryl, 3,4-dimethoxybenzyl, 3,4-dihydroxybenzyl, 2-methoxystyryl, 3,4-dihydroxystyryl, 2-hydroxystyryl, phenyl, 4-chlorostyryl, m-anisyl, 4-isopropylphenyl, 4-vinylphenyl, 4-fluorophenyl, 4-bromophenyl, 3,4-dimethoxystyryl, 4-hydroxyphenyl, styryl, 3,4-dimethylphenyl, 3-fluoro-4-methylphenyl, 3-bromo-4-methylphenyl, 3-iodo-4-methylphenyl, 3,4-dichlorophenyl, 4-biphenyl, 3,4-difluorophenyl, m-tolyl, benzyl, phenethyl, 3-methoxy-4-methylphenyl, 3-phenylpropyl, 4-butylphenyl, 3,5-dimethylphenyl, 3,5-bis(trifluoromethyl)-phenyl, 3,4-dimethoxyphenyl, 4'-ethyl-4-biphenyl, 3,4,5-trimethoxyphenyl, 3,4,5-triethoxyphenyl, propyl, hexyl, 2-propyl, 2-butyl, isobutyl, 2-methylbutyl, isovaleryl, 1-propenyl, 2-propenyl, 3-hepten-3-yl, p-tolyl, p-anisyl, t-butyl, cyclohexyl, cyclohexylmethyl, 3-cyclohexylpropyl, cycloheptyl, methyl, 2-methylcyclopropyl, cyclobutyl, cyclopentyl, 2-cyclopentylethyl, 2-furyl, 2-cyclohexylethyl, 4-methylcyclohexyl, 4-t-butylcyclohexyl, 4-methylcyclohexanemethyl, 2-buten-2-yl, 2-norboranemethyl, 1-adamantanemethyl, or 2-thienyl;

X is a nitrogen atom or a sulfur atom; and

Y is a hydrogen atom or methyl.

Because libraries can be screened while still bound to the resin, additional embodiments of the invention include any of the above-described libraries bound to a solid-phase resin. The compounds in such libraries would be resin-bound through the amide in the above Formula. In such instances, one hydrogen atom of the amide would be absent. The resins to which such compounds can be bound are functionalized amine resins, solid-phase resins cross-linked with amino groups, in which case it would be appreciated by those in the art that the amine function is cleaved from the resin during standard hydrogen fluoride (HF) cleavage procedures and retained with the subject compounds.

In the above Formula the stereochemistry of the chiral $R^1$ through $R^4$ groups can independently be in the R or S configuration, or a mixture of the two. For instance, as will be described in further detail below the $R^1$ and $R^3$ groups are the side chains of the α-carbon of various amino acids. The amino acids can be in the L- or D-configuration, resulting in the same R group, varying only in its stereochemistry.

In the above Formulae, the term "$C_1$ to $C_{10}$ alkyl" denotes such radicals as methyl, ethyl, n-propyl, isopropyl, n-butyl, sec-butyl, tert-butyl, amyl, tert-amyl, hexyl, heptyl and the like. A preferred "$C_1$ to $C_{10}$ alkyl" group is methyl.

The term "$C_2$ to $C_{10}$ alkenyl" denotes such radicals as vinyl, allyl, 2-butenyl, 3-butenyl, 2-pentenyl, 1-propenyl, 2-propenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_{10}$ alkynyl" denotes such radicals as ethynyl, propynyl, butynyl, pentynyl, hexynyl, heptynyl, as well as di- and tri-ynes.

The term "$C_1$ to $C_{10}$ substituted alkyl," "$C_2$ to $C_{10}$ substituted alkenyl," and "$C_2$ to $C_{10}$ substituted alkynyl," denotes that the above $C_1$ to $C_{10}$ alkyl groups and $C_2$ to $C_{10}$ alkenyl and alkynyl groups are substituted by one or more, and preferably one or two, halogen, hydroxy, protected hydroxy, $C_3$ to $C_7$ cycloalkyl, $C_3$ to $C_7$ substituted cycloalkyl, naphthyl, substituted naphthyl, adamantyl, abietyl, thiofuranyl, indolyl, substituted indolyl, amino, protected amino, (monosubstituted)amino, protected (monosubstituted)amino, (disubstituted)amino, guanidino, (monosubstituted)guanidino, (disubstituted)guanidino, (trisubstituted)guanidino, imidazolyl, pyrolidinyl, pyridinyl, $C_1$ to $C_7$ acyloxy, nitro, heterocycle, substituted heterocycle, $C_1$ to $C_4$ alkyl ester, carboxy, protected carboxy, carbamoyl, carbamoyloxy, carboxamide, protected carboxamide, cyano, methylsulfonylamino, methylsulfonyl, sulfurhydryl, $C_1$ to $C_4$ alkylthio, $C_1$ to $C_4$ alkyl sulfonyl or $C_1$ to $C_4$ alkoxy groups. The substituted alkyl groups may be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allylcaroxybonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(isopropyl), 2-carbamoyloxyethyl chloroethyl, bromoethyl, fluoroethyl, iodoethyl, chloropropyl, bromopropyl, fluoropropyl, iodopropyl, naphthylmethyl and the like.

In preferred embodiments of the subject invention, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, or $C_2$ to $C_{10}$ substituted alkynyl preferably $C_1$ to $C_7$, respectively, and more preferably, $C_1$ to $C_6$. However, it would be appreciated to those of skill in the art that one or a few carbons could be added to an alkyl, alkenyl, alkynyl, substituted or unsubstituted, without substantially modifying the structure and function of the subject compounds and that, therefore, such additions would not depart from the spirit of the invention.

The term "$C_1$ to $C_4$ alkoxy" as used herein denotes groups such as methoxy, ethoxy, n-propoxy, isopropoxy, n-butoxy, t-butoxy and like groups. A preferred $C_1$ to $C_4$ alkoxy group is methoxy.

The term "$C_1$ to $C_7$ acyloxy" denotes herein groups such as formyloxy, acetoxy, propanoyloxy, butanoyloxy, pentanoyloxy, hexanoyloxy, heptanoyloxy, and the like.

Similarly, the term "$C_1$ to $C_7$ acyl" encompasses groups such as formyl, acetyl, propionoyl, butyroyl, pentanoyl, hexanoyl, heptanoyl, benzoyl and the like.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, phenyl, substituted phenyl, heterocycle, substituted heterocycle, $C_1$ to $C_{10}$ alkyl, $C_1$ to $C_4$ alkoxy, carboxy, protected carboxy, amino, or protected amino.

The substituent term "$C_3$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_3$ to $C_7$ cycloalkenyl" denotes the above $C_3$ to $C_7$ cycloalkenyl rings substituted by a $C_1$ to $C_{10}$ alkyl radical, halogen, hydroxy, protected hydroxy, $C_1$ to $C_4$ alkoxy, carboxy, protected carboxy, amino, or protected amino.

The term "heterocyclic ring" or "heterocycle"denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred. Preferred heterocyclic rings include pyridino, pyrimidino, and pyrazino, furano, and thiofurano rings. The heterocyles can be substituted or unsubstituted as, for example, with such substituents as those described in relation to substituted phenyl or substituted naphthyl and when substituted are termed "substituted heterocyclic ring" or "substituted heterocycle."

The term "$C_7$ to $C_{16}$ phenylalkyl" denotes a $C_1$ to $C_{10}$ alkyl group substituted at any position by a phenyl ring. Examples of such a group include benzyl, 2-phenylethyl, 3-phenyl-(n-prop-1-yl), 4-phenyl-(-hex-1-yl), 3-phenyl-(n-am-2-yl), 3-phenyl-(sec-butyl), and the like. A preferred group is the benzyl group.

The term "$C_7$ to $C_{16}$ substituted phenylalkyl" denotes a $C_7$ to $C_{16}$ arylalkyl group substituted on the $C_1$ to $C_{10}$ alkyl portion with one or more, and preferably one or two, groups chosen from halogen, hydroxy, protected hydroxy, keto, $C_2$ to $C_3$ cyclic ketal, phenyl, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_{10}$ alkyl, $C_1$ to $C_6$ substituted alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, amino, (monosubstituted)amino, (disubstituted)amino, a N-(methylsulfonylamino) group, or a phenyl group, substituted or unsubstituted, for a resulting biphenyl group. When either the $C_1$ to $C_{10}$ alkyl portion or the phenyl portion or both are mono- or di-substituted the substituents can be the same or different.

Examples of the term "$C_7$ to $C_{16}$ substituted henylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethylphenyl)-3-(aminomethyl)(n-pent-2-yl), 5-phenyl-3-keto-(n-pent-1-yl), 4-(4-aminophenyl)-4-(1,4-oxetanyl)(n-but-1-yl), and the like.

The term "$C_7$ to $C_{16}$ phenylalkenyl" denotes a $C_2$ to $C_{10}$ alkenyl group substituted at any position by a phenyl ring. A preferred $C_7$ to $C_{16}$ phenylalkenyl is styryl. The term "$C_7$ to $C_{16}$ substituted phenylalkenyl" denotes a $C_7$ to $C_{16}$ arylalkyl group substituted on the $C_1$ to $C_{10}$ alkenyl portion and/or the phenyl group may be substituted with 1 or 2 substituents. Substituents can the same as those as defined above in relation to $C_7$ to $C_{16}$ phenylalkyl and $C_7$ to $C_{16}$ substituted phenylalkyl. A preferred $C_7$ to $C_{16}$ substituted phenylalkenyl is 3-(4-nitrophenyl)-2-propenyl.

The term "substituted phenyl" specifies a phenyl group substituted with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_4$ alkoxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted) amino, trifluoromethyl, N-(methylsulfonylamino), or phenyl, substituted or unsubstituted, such that, for example, a biphenyl results.

Examples of the term "substituted phenyl" includes a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected-hydroxy derivatives thereof and the like; a nitrophenyl group such as 3-or 4-nitrophenyl; a cyanophenyl group for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-prop-1-yl)phenyl and the like; a mono or di(alkoxyl)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like; 3-or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "substituted benzyl" means a benzyl group substituted with one or more, and preferably one or two, moieties chosen from the same groups as provided with reference to "substituted phenyl." Examples of substituted benzyl include 4-bromobenzyl, 4-chlorobenzyl, 4-fluorobenzyl, 4-ethoxybenzyl and the like.

The term "substituted naphthyl" specifies a naphthyl group substituted with one or more, and preferably one or two, moieties chosen from the groups consisting of halogen, hydroxy, protected hydroxy, cyano, nitro, $C_1$ to $C_{10}$ alkyl, $C_1$ to $C_4$ alkoxy, carboxy, protected carboxy, carboxymethyl, protected carboxymethyl, hydroxymethyl, protected hydroxymethyl, amino, protected amino,(monosubstituted) amino, protected (monosubstituted)amino, (disubstituted) amino trifluoromethyl or N-(methylsulfonylamino). Examples of substituted naphthyl include 2-(methoxy)-naphthyl and 4-(methoxy) naphthyl.

The term "substituted indolyl" specifies a indolyl group substituted, either at the nitrogen or carbon, or both, with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_{10}$ alkenyl, $C_7$ to $C_{16}$ phenylalkyl, $C_7$ to $C_{16}$ substituted phenylalkyl, $C_1$ to $C_6$ alkoxy, carboxy, protected carboxy, carboxymethyl, protected carboxymethyl, hydroxymethyl, protected hydroxymethyl, amino, protected amino, monosubstituted amino, or disubstituted amino.

Examples of the term "substituted indolyl" includes such groups as 6-fluoro, 5-fluoro, 5-bromo, 5-hydroxy, 5-methyl, 6-methyl, 7-methyl, 1-methyl, 1-ethyl, 1-benzyl, 1-napth-2-ylmethyl, and the like. An example of a disubstituted indolyl is 1-methyl-5-methyl indolyl.

The terms "halo" and "halogen" refer to the fluoro, chloro, bromo or iodo groups.

The term "(monosubstituted)amino" refers to an amino group with one substituent chosen from the groups consisting of phenyl, substituted phenyl, $C_1$ to $C_{10}$ alkyl, and $C_7$ to $C_{16}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents chosen from the group consisting of phenyl, substituted phenyl, $C_1$ to $C_{10}$ alkyl, and $C_7$ to $C_{16}$ arylalkyl wherein the latter three substituent terms are as described above. The two substituents can be the same or different.

The terms "(monosubstituted)guanidino," "(disubstituted)guanidino," and "(trisubstituted)guanidino" are where the guanidino groups is substituted with one, two, or three substituents, respectively. The substituents can be any of those as defined above in relation to (monosubstituted)amino and (disubstituted)amino and, where more than one substituent is present, the substituents can be the same or different.

The term "amino-protecting group" as used herein refers to substituents of the amino group commonly employed to block or protect the amino functionality while reacting other functional groups on the amine component. The term "protected (monosubstituted)amino" means there is an amino-protecting group on the monosubstituted amino nitrogen atom. In addition, the term "protected carboxamide" means there is an amino-protecting group replacing the proton so that there is no N-alkylation. Examples of such amino-protecting groups include the formyl ("For") group, the trityl group (Trt), the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl(2)oxycarbonyl ("Bpoc"), 2-phenylpropyl(2)oxycarbonyl ("Poc"), 2-(4-xenyl)isopropoxycarbonyl, 1,1-diphenylethyl(1)-oxycarbonyl, 1,1-diphenylpropyl(1)oxycarbonyl, 2-(3,5-dimethoxyphenyl)propyl(2)oxycarbonyl ("Ddz"), 2-(p-oluyl)propyl(2)oxycarbonyl, cyclopentanyloxycarbonyl, 1-methylcyclopentanyloxycarbonyl, cyclohexanyloxy-carbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluoroenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benz-isoxalylmethoxycarbonyl, 4-acetoxybenzyloxycarbonyl, 2,2,2-trichloroethoxycarbonyl, 2-ethynyl(2)propoxy-carbonyl, cyclopropyl-methoxycarbonyl, isobornyl-oxycarbonyl, 1-piperidyloxycarbonyl, benzyloxycarbonyl ("Z"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2

-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like; the benzoylmethylsulfonyl group, dithiasuccinoyl ("Dts"), the 2-(nitro)phenylsulfenyl group ("Nps"), the diphenylphosphine oxide group, and like amino-protecting groups.

The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc and Fmoc. Further examples of amino-protecting groups embraced to by the above term are well known in organic synthesis and the peptide art and are described by, for example, T. W. Greene and P. G. M.

Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-timethoxytrityl, 2-phenylprop-2-yl, trimethylsilyl, t-butyldimethylsilyl, 2,2,2-trichloroethyl, β-(trimethylsilyl)ethyl, β-(di(n-butyl)methylsilyl)ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the imidazol-pyrido-indoles or imidazol-pyrido-benzothiophenes. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The substituent term "$C_1$ to $C_4$ alkylthio" refers to sulfide groups such as methylthio, ethylthio, n-propylthio, iso-propylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, iso-propylsulfoxide, n-butylsulfoxide, sec-butylsulfoxide, and the like.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

Phenylthio, phenyl sulfoxide, and phenylsulfonyl compounds are known in the art and these terms have their art recognized definition. By "substituted phenylthio," "substituted phenyl sulfoxide," and "substituted phenylsulfonyl" is meant that the phenyl can be substituted as described above in relation to "substituted phenyl."

The substituent terms "cyclic $C_2$ to $C_{10}$ alkylene," "substituted cyclic $C_2$ to $C_{10}$ alkylene," "cyclic $C_2$ to $C_{10}$ heteroalkylene," and "substituted cyclic $C_2$ to $C_{10}$ heteroalkylene," defines such a cyclic group bonded ("fused") to the phenyl radical. The cyclic group may be saturated or contain one or two double bonds. Furthermore, the cyclic group may have one or two methylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, keto, ketal, $C_1$ to $C_4$ alkoxycarbonyl, formyl, $C_2$ to $C_4$ alkanoyl, $C_1$ to $C_{10}$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the benzene radical can contain two to ten ring members, but it preferably contains four to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indanyl. An example of a cyclic group which can be fused to a phenyl radical which has two oxygen atoms and which is fully saturated is dioxanyl. Examples of fused cyclic groups which each contain one oxygen atom and one or two double bonds are when the phenyl ring is fused to a furo, pyrano, dihydrofurano, or dihydropyrano ring. Examples of cyclic groups which each have one nitrogen atom and contain one or two double more double bonds are when the phenyl is fused to a pyridino or pyrano ring. An example of a fused ring system having one nitrogen and two phenyl radicals is a carbozoyl group. Examples of cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring.

One or more of the imidazol-pyrido-indole or imidazol-pyrido-benzothiophenes within a given library may be present as a pharmaceutically acceptable salt. The term "pharmaceutically-acceptable salt" encompasses those salts that form with the carboxylate anions and include salts formed with the organic and inorganic cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicylic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)ammonium, phenylethylbenzylammonium, dibebenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. A preferred cation for the carboxylate anion is the sodium cation.

The compounds of the above Formula can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more imidazol-pyrido-indoles or imidazol-pyrido-benzothiophenes can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, iso-propoxymethyl and the like; the $\alpha$-($C_1$ to $C_4$) alkoxyethyl groups, for example methoxyethyl, ethoxyethyl, propxyethyl, iso-propoxyethyl, and the like; the 2-oxo-1,3-diosolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, pivaloyloxyethyl, $\alpha$-acetoxymethyl, and the like; the ethoxycarbonyl-1-methyl group; the $\alpha$-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

As used herein, a chemical or combinatorial "library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). The libraries can be screened in any variety of assays, such as those detailed below as well as others useful for assessing the biological activity of imidazol-pyrido-indoles or imidazol-pyrido-benzothiophenes. The libraries will generally have at least one active compound and are generally prepared in such that the compounds are in equimolar quantities. As will be described in further detail, a library of approximately 24,000 imidazol-pyrido-indole and imidazol-pyrido-benzothiophene compounds was prepared. It should be appreciated, however, that such libraries can comprise several smaller "sub-libraries" or sets of mixtures of compounds, depending on the format of preparation and the varying R groups. Sublibraries are described in further detail below.

"Combinatorial chemistry" or "combinatorial synthesis" refers to the parallel synthesis of diverse compounds by sequential addition of reagents which leads to the generation of large chemical libraries having molecular diversity. Combinatorial chemistry, therefore, involves the systematic and repetitive, covalent connection of a set of different "building blocks" of varying structures to yield large arrays of diverse molecular entities.

The imidazol-pyrido-indole and imidazol-pyrido-benzothiophene libraries containing the compounds of Formula I can be prepared as follows and such methods of preparation are also provided by the subject invention. Unexpectedly, very diverse libraries containing complex imidazol-pyrido-indole and imidazol-pyrido-benzothiophene compounds, can be prepared by condensing two or more resin-bound acylated dipeptides having as their C-terminal amino acid a tryptophan derivative or a $\beta$-(3-benzothienyl)alanine derivative. Following the general reaction scheme below, the condensation can be done by applying Bischler-Napieralski condensation reaction conditions, such as phosphorous oxychloride ($POCl_3$) in anhydrous dioxane, to resin bound acylated dipeptides which can subsequently be cleaved from the resin, using standard hydrogen fluoride (HF) procedures.

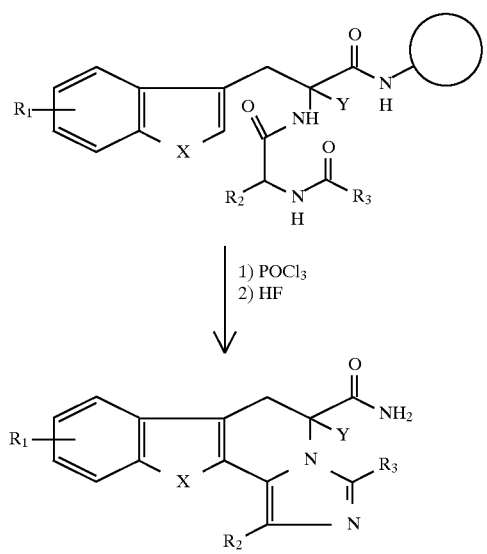

More specifically, an amino-protected first amino acid which is a tryptophan and/or $\beta$-(3-benzothienyl)alanine derivative (having side chain $R^1$) is coupled to an amine-functionalized resin. By "amino-protected" is meant a first amino acid having a labile amino-protecting group as defined above. A preferred amino-protecting group is Boc. The term "functionalized amine resin" means any solid-phase resin having amine functional groups introduced into the resin, as is common in the art. An example of such resin is 4-methylbenzhydrylamine-copoly(styrene-1% divinylbenzene)(MBHA).

Any variety of Trp and Ala derivatives can be used as encompassed by the above $R^1$ groups. Exemplary derivatives are those used to prepare the library provided in Example I, including β-(3-benzo-thienyl)-Ala, β-(3-benzo-thienyl)-D-Ala, 6-fluoro-DL-Trp, 5-fluoro-DL-Trp, 5-bromo-DL-Trp, 5-hydroxy-DL-Trp, 1-methyl-DL-Trp, 5-methyl-DL-Trp hydrate, N-α-methyl-DL-Trp, 6-methyl-DL-Trp, 7-methyl-DL-Trp, Trp, and D-Trp.

In the next step, the labile amino-protecting group is removed from the resin-bound first amino acid and a second protected amino acid (having side chain $R^2$) is added using traditional solid-phase peptide chemistry. The second amino acid is protected with an amino-protecting group, and where necessary, a side chain protecting group. Any variety of second amino acids can be used. As described in the ensuing Example, twenty-five amino acids were used to generate different $R^2$ groups, including Ala, Phe, Gly, His(Dnp), Lys(Cbz), Met(O), Gln, Tyr(Brz), α-Aba, Nve, Nle, Orn (Cbz), Phg, Nap, Cha, Met-$O_2$, p$NO_2$-Phe, pCl-Phe, pF-Phe, 3-pyridyl-Ala, 2-thienyl-Ala, t-Bu-Gly, Tic, homopro, and O-Et-Tyr. Abbreviations for these amino acids are those commonly known in the field. The abbreviations and the respective side chains of the amino acids are as follows:

TABLE I

| AMINO ACID NAME | | |
|---|---|---|
| FULL | CODE | SIDE CHAIN $R^2$ |
| Glycine | Gly | —H |
| Alanine | Ala | —$CH_3$ |
| Lysine | Lys | —$(CH_2)_4NH_2$ |
| Phenylalanine | Phe | 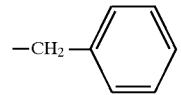 |
| p-Nitro-Phenylalanine | p$No_2$—Phe | 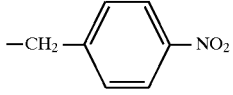 |
| p-Chloro-Phenylalanine | pCl—Phe | 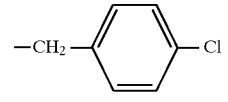 |
| p-Fluoro-Phenylalanine | pF—Phe | 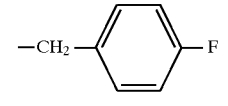 |
| Tyrosine | Tyr | 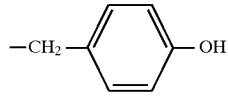 |
| O-Ethyl-Tyrosine | O—Et—Tyr | 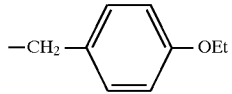 |

TABLE I-continued

| AMINO ACID NAME | | |
|---|---|---|
| FULL | CODE | SIDE CHAIN $R^2$ |
| Norvaline | Nva | —$CH_2CH_2CH_3$ |
| Norleucine | Nle | —$CH_2CH_2CH_2CH_3$ |
| Napthylalanine | Nap | 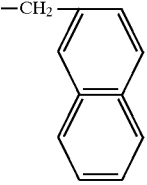 |
| Cyclohexylalanine | Cha | 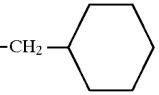 |
| Methionine | Met | —$CH_2CH_2$—S—$CH_3$ |
| Methionine Sulfone | Met—$O_2$ | —$CH_2CH_2S(O_2)CH_3$ |
| Glutamine | Gln | —$CH_2CH_2C(O)NH_2$ |
| Histidine | His | 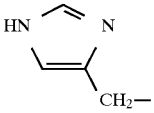 |
| Phenylglycine | Phg | 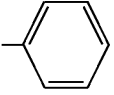 |
| α-Aminobutyric Acid | α-Aba | —$CH_2CH_3$ |
| Ornithine | Orn | —$CH_2CH_2CH_2NH_2$ |
| 3-Pyridyl-Alanine | 3-pyridyl-Ala | 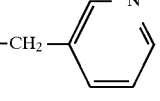 |
| 2-Thienyl-Alanine | 2-thienyl-Ala | 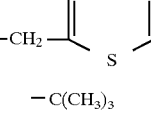 |
| tert-Butyl-Glycine | t-Bu—Gly | —$C(CH_3)_3$ |
| 1,2,3,4-Tetrahydroisoquinoline-3-Carboxylic Acid | Tic | 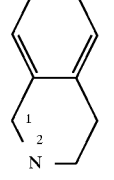 |
| homoProline | homoPro | 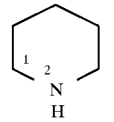 |

** in conjunction with C1 & N2

After completion of coupling, the amino-terminus of the resin-bound dipeptide is then deprotected and the dipeptide acylated with one of a wide range of carboxylic acids to obtain an acylated resin-bound dipeptide. Exemplary carboxylic acids include 1-phenyl-1-cyclopropane-carboxylic acid, 2-phenylbutyric acid, 3-phenylbutyric acid, m-tolylacetic acid, 3-fluorophenylacetic acid, 3-bromophenylacetic acid, (α,α,α-trifluoro-m-tolyl)acetic acid, p-tolylacetic acid, 4-fluorophenylacetic acid, 3-methoxyphenylacetic acid, 4-bromophenylacetic acid, 4-methoxyphenylacetic acid, 4-ethoxyphenylacetic acid, 4-isobutyl-α-methylphenylacetic acid, 3,4-dichlorophenylacetic acid, 3,5-bis(trifluoromethyl) phenylacetic acid, 3-(3,4-dimethoxyphenyl)-propionic acid, 4-biphenylacetic acid, α-methylcinnamic acid, 2-(trifluoromethyl)cinnamic acid, (3,4-dimethoxyphenyl) acetic acid, 3,4-(methylenedioxy)-phenylacetic acid, 2-methoxycinnamic acid, 3,4-(methylenedioxy)-cinnamic acid, 2-hydroxycinnamic acid, benzoic acid, 4-chlorocinnamic acid, m-anisic acid, 4-isopropylbenzoic acid, 4-vinylbenzoic acid, 4-fluorobenzoic acid, 4-bromobenzoic acid, 3,4-dimethoxycinnamic acid, 4-hydroxybenzoic acid, trans-cinnamic acid, 3,4-dimethylbenzoic acid, 3-fluoro-4-methylbenzoic acid, 3-bromo-4-methylbenzoic acid, 3-iodo-4-methylbenzoic acid, 3,4-dichlorobenzoic acid, 4-biphenylcarboxylic acid, 3,4-diflurobenzoic acid, m-toluic acid, phenylacetic acid, hydrocinnamic acid, 3-methoxy-4-methylbenzoic acid, 4-phenylbutyric acid, 4-butylbenzoic acid, 3,5-dimethylbenzoic acid, 3,5-bis(trifluoromethyl)-benzoic acid, 3,4-dimethoxybenzoic acid, 4-ethyl-4-biphenylcarboxylic acid, 3,4,5-trimethoxybenzoic acid, 3,4,5-triethoxybenzoic acid, butyric acid, heptanoic acid, isobutyric acid, (±)-2-methylbutyric acid, isovaleric acid, 3-methylvaleric acid, 4-methylvaleric acid, crotonic acid, vinylacetic acid, 2-ethyl-2-hexenoic acid, p-toluic acid, p-anisic acid, trimethylacetic acid, cyclohexanecarboxylic acid, cyclohexylacetic acid, cyclohexanebutyric acid, cycloheptanecarboxylic acid, acetic acid, 2-methylcyclopropanecarboxylic acid, cyclobutanecarboxylic acid, cyclopentanecarboxylic acid, 3-cyclopentylpropionic acid, 2-furioc acid, cyclohexanepropionic acid, 4-methyl-1-cyclohexanecarboxylic acid, 4-tert-butyl-cyclohexanecarboxylic acid, 4-methylcyclohexaneacetic acid, tiglic acid, 2-norbornaneacetic acid, 1-adamantaneacetic acid, and 2-thiophenecarboxylic acid.

Following acylation, side-chain protecting groups can be removed, as for example, by low HF procedures. The final step in the combinatorial synthesis is, as shown in the above reaction scheme, ring closure by Bischler-Napieralski condensation. The condensation can be done with (phosphorous oxychloride ($POCl_3$) (as depicted above), phosphorous chloride ($PCl_3$), or phosphorous pentoxide ($P_2O_5$). Any one of these reagents should be used in the presence of a nonaromatic solvent, such as 1,4-dioxane. After condensation, the imidazole compounds can be cleaved from the resin using standard HF procedures.

The subject libraries are useful for rapidly preparing and screening a wide array of compounds and have utility in optimization and drug discovery programs. The libraries can be screened while still on the resin or after cleavage. With the subject invention, the nonsupport-bound library mixtures were screened in solution in a radio-receptor inhibition assay and an anti-bacterial assay described in detail below. Deconvolution of highly active mixtures can then be carried out by iterative, or positional scanning methods. These techniques, the iterative approach or the positional scanning approach, can be utilized for finding other active compounds within the libraries of the present invention using any one of the below-described assays or others well known in the art.

The iterative approach is well-known and is set forth in general in Houghten et al., *Nature,* 354, 84–86 (1991) and Dooley et al., *Science,* 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various libraries as described, for example, in R. Houghten et al. PCT/US91/08694 and U.S. Pat. No. 5,556,762, both of which are incorporated herein by reference. The positional scanning approach is used as described below in the preparation and screening of the libraries. In the positional scanning approach sublibraries are made defining only one variable with each set of sublibraries- and all possible sublibraries with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the new imidazol-pyrido-indoles or imidazol-pyrido-benzothiophenes, as well as methods of using the same are included within the scope of the present invention. The new imidazol-pyrido-indoles or imidazol-pyrido-benzothiophenes compounds of the present invention can be used for a variety of purposes and indications and as medicaments for such purposes and indications.

For instance, as shown in Example III imidazol-pyrido-indoles or imidazol-pyrido-benzothiophenes of the present invention have antimicrobial activity. Thus the compounds of the present invention can be used to treat infections. The ability of the compounds to inhibit bacterial growth can be determined by methods well known in the art. An exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 µl of the culture solution using serial dilutions (e.g., $10^{-2}$, $10^{-2}$ and $10^{-4}$) onto solid agar plates. In 96-well tissue culture plates imidazol-pyrido-indoles or imidazol-pyrido-benzothiophenes, individually or in mixtures, are added to the bacterial suspension at concentrations derived from serial two-fold dilutions ranging from 1500 to 2.9 µg/ml. The plates are incubated overnight at 37° C. and the growth determined at each concentration by $OD_{620}$ nM. The $IC_{50}$ (the concentration necessary to inhibit 50% of the growth of the bacteria) can then be calculated.

Additional assays can be, and have been, used to test the biological activity of the instant imidazol-pyrido-indoles or imidazol-pyrido-benzothiophenes. One such assay is the competitive enzyme-linked immunoabsorbent assay (ELISA). One competitive ELISA method which can be used is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 µl. After blocking, 25 µl of a 1.0 mg/ml solution of each imidazol-pyrido-indole or imidazol-pyrido-benzothiophene mixture of a synthetic combinatorial library (or individual compound) is added, followed by MAb 125-10F3 (Appel et al., supra) (25 µl per well). The MAb is added at a fixed dilution in which the imidazol-pyrido-indole or imidazol-pyrido-benzothiophene in solution effectively competes for MAb binding with the antigenic peptide adsorbed to the plate. The remaining steps are the same as for direct ELISA. The concentration of compound necessary to inhibit 50% of the MAb binding to the control peptide on the plate ($IC_{50}$) is determined by serial dilutions.

Alternative screening can be, and has been, done with radio-receptor assays as provided in Example III and FIGS. 1 and 2. The radio-receptor assay, can be selective for any one of the µ, κ, or δ opiate receptors. Therefore, the compounds of the present invention are useful in vitro for the diagnosis of relevant opioid receptor subtypes, such as µ, in the brain and other tissue samples. Similarly, the compounds can be used in vivo diagnostically to localize opioid receptor subtypes. The radio-receptor assays are also an indication of the compounds' analgesic properties as described, for example, in Dooley et al., *Proc. Natl. Acad. Sci.*, 90:10811–10815 (1993). Additionally, such compounds can be tested in a σ receptor assay. Ligands for the σ receptor can be useful as antipsychotic agents, as described in Abou-Gharbia et al., *Annual Reports in Medicinal Chemistry*, 28:1–10 (1993).

The radio-receptor assay can be done as follows. Particulate membranes can be prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall® RC$_5$C SA-600: Du Pont, Wilmington, Del.) (16,000 rpm) for 10 mins. The pellets are resuspended in fresh Tris-HCl buffer and incubated at 37° C. for 40 mins. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in M. M. Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$, Gly-ol$^5$] enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 µg/ml of imidazol-pyrido-indole or imidazol-pyrido-benzothiophene, individually or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the compounds, individually or in mixtures. $IC_{50}$ values (the concentration necessary to inhibit 50% of $^3$H-DAMGO binding) are then calculated. As opposed to this µ receptor selective assay, assays selective for κ receptors can be carried out using [$^3$H]-U69,593 (3 nM, specific activity 62 Ci/mmol) as radioligand. Assays selective for δ opiate receptors can be carried out using tritiated DSLET ([D-Ser$^2$, D-Leu$^5$]-threonine-enkephalin) as radioligand. Similarly, assays for the σ receptor assay are the same as the µ assay but use radiolabeled pentazocine as ligand.

As pharmaceutical compositions for treating infections, pain, or other indications known to be treatable by imidazol-pyrido-indoles or imidazol-pyrido-benzothiophenes, the compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active compound. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

INTRODUCTION

When using either the iterative or positional scanning approach to the synthesis of the instant libraries, it is necessary at some point to expose either the solid phase alone or the solid phase bound to one or two amino acids, to a mixture of reactive subunits. Such subunits can be the first or second amino acid, or an activated carboxylic acid residue. As each individual subunit in the mixture may react at varying rates with the solid phase or the molecule bound to the solid phase, it is advantageous to know the relative reaction rate of each subunit. Once such relative rates are known, the concentration of each reactive subunit can be adjusted accordingly in order to have approximately equimolar amounts of each reactive subunit couple with either the bare solid support or the molecule bound to the support. (For a further discussion of this point, see J. M. Ostresh et al., *Biopolymers,* 34:1661–1689 (1994), herein incorporated by reference).

The theory underpinning the methodology for determining the relative reaction rates used by Ostresh et al. in the above-mentioned *Biopolymers* article is set forth below.

Assuming that a large excess of the amino acid to be reacted with the Peptide which in turn is bound to the solid support is used, then the rate of such a reaction for amino acid 1 and amino acid 2 is expressed in Equations (1) and (2) below, respectively:

$$[\text{Peptide-}AA_1] = k_{AA-1} \times [AA_1] \quad (1)$$

wherein:

"Peptide"=Ala-Phe-Leu-;

$AA_1$=baseline amino acid; and $k_{AA-1}$=reaction constant of $AA_1$ with Peptide.

$$[\text{Peptide-}AA_2] = k_{AA-2} \times [AA_2] \quad (2)$$

wherein:

"Peptide"=Ala-Phe-Leu-;

$AA_2$=amino acid whose reaction rate with Peptide is to be compared to $AA_1$; and $k_{AA-2}$=reaction rate of $AA_2$ with the Peptide.

If $k_{AA-1}$ and $k_{AA-2}$ are different, then for any given period of time, more of the AA with the slower rate must be added to the mixture of reactive subunits so that the Peptide attached to the solid support will have reacted at that step with approximately equal amounts of $AA_1$ and $AA_2$. Thus, only relative rates are of importance, and can be determined using the following equations:

$$\frac{k_{AA-1}}{k_{AA-2}} = \frac{[\text{peptide}-AA_1] \times [AA_2]}{[\text{peptide}-AA_2] \times [AA_1]} \quad (3)$$

In order to simplify the calculations, a ten fold molar excess of both $AA_1$ and $AA_2$ are used in experiments coupling the AA in question to the solid support "Peptide"; allowing Equation 3 to be simplified to Equation 4:

$$\frac{k_{AA-1}}{k_{AA-2}} = \frac{[\text{peptide}-AA_1]}{[\text{peptide}-AA_2]} \quad (4)$$

on the assumption that $[AA_1]=[AA_2]$.

In order to determine the proper ratio of concentrations of $AA_1$ and $AA_2$ to use in a reaction mixture; Equations (3) and (4) are solved for $[AA_1]$ and $[AA_2]$ to give Equation (5):

$$\frac{[AA_2]}{[AA_1]} = \frac{k_{AA-1}[\text{peptide}-AA_2]}{k_{AA-2}[\text{peptide}-AA_1]} \quad (5)$$

Since equimolar concentrations of Peptide-$AA_1$ and Peptide-$AA_2$ are desired equation (5) simplifies to Equation (6):

$$\frac{[AA_2]}{[AA_1]} = \frac{k_{AA-1}}{k_{AA-2}} \quad (6)$$

The ratio in Equation (6) was determined using the following modification of the *Biopolymers* article procedure. Thus, instead of cleaving and hydrolysing the peptide with 6N hydrochloric acid, equimolar amounts of Peptide-$AA_1$ and Peptide-$AA_2$, each bound separately to the same type of solid support used in the reactions of $AA_1$ and $AA_2$, were mixed with the reaction mixtures. The peptides were then cleaved and analyzed by HPLC (5–65% B in 30 minutes, Vydac 218TP54, A:0.05% TFA/$H_2O$, B:0.05% TFA/ACN, 214 nm).

The relative ratios for the reactive subunits determined by the above methodology are set forth below in Tables 2 and 3:

TABLE 2

Carboxylic Acid Ratios

| No. | ITEM | RATIO |
|---|---|---|
| 1 | 1-phenyl-1-cyclopropanecarboxylic acid | 1.00 |
| 2 | 2-phenylbutyric acid | 1.20 |
| 3 | 3-phenylbutyric acid | 2.60 |
| 4 | m-tolylacetic acid | 1.80 |
| 5 | 3-fluorophenylacetic acid | 0.84 |
| 6 | 3-bromophenylacetic acid | 0.61 |
| 7 | (α-α-α-trifluoro-m-tolyl)acetic acid | 0.61 |
| 8 | p-tolylacetic acid | 1.36 |
| 9 | 4-fluorophenylacetic acid | 1.04 |
| 10 | 3-methoxyphenylacetic acid | 1.17 |
| 11 | 4-bromophenylacetic acid | 0.88 |
| 12 | 4-methoxyphenylacetic acid | 1.80 |
| 13 | 4-ethoxyphenylacetic acid | 1.40 |
| 14 | 4-isobutyl-α-methylphenylacetic acid | 1.70 |
| 15 | 3,4-dichlorophenylacetic acid | 0.81 |
| 16 | 3,5-bis(trifluoromethyl)-phenylacetic acid | 0.50 |
| 17 | 3-(3,4-dimethoxyphenyl)-propionic acid | 2.20 |
| 18 | 4-biphenylacetic acid | 1.40 |
| 19 | α-methylcinnamic acid | 1.95 |
| 20 | 2-(trifluoromethyl)cinnamic acid | 1.03 |
| 21 | (3,4-dimethoxyphenyl)acetic acid | 1.44 |
| 22 | 3,4-(methylenedioxy)-phenylacetic acid | 1.27 |
| 23 | 2-methoxycinnamic acid | 5.60 |
| 24 | 3,4-(methylenedioxy)cinnamic acid | 10.40 |
| 25 | 2-hydroxycinnamic acid | 4.90 |
| 26 | benzoic acid | 1.28 |
| 27 | 4-chlorocinnamic acid | 2.95 |
| 28 | m-anisic acid | 1.52 |
| 29 | 4-isopropylbenzoic acid | 3.00 |
| 30 | 4-vinylbenzoic acid | 1.50 |
| 31 | 4-fluorobenzoic acid | 1.22 |
| 32 | 4-bromobenzoic acid | 0.59 |
| 33 | 3,4-dimethoxycinnamic acid | 7.27 |
| 34 | 4-hydroxybenzoic acid | 7.61 |
| 35 | trans-cinnamic acid | 4.20 |
| 36 | 3,4-dimethylbenzoic acid | 2.44 |
| 37 | 3-fluoro-4-methylbenzoic acid | 0.75 |
| 38 | 3-bromo-4-methylbenzoic acid | 0.86 |
| 39 | 3-iodo-4-methylbenzoic acid | 0.84 |
| 40 | 3,4-dichlorobenzoic acid | 0.39 |
| 41 | 4-biphenylcarboxylic acid | 5.10 |
| 42 | 3,4-difluorobenzoic acid | 0.45 |
| 43 | m-toluic acid | 1.60 |
| 44 | phenylacetic acid | 1.00 |
| 45 | hydrocinnamic acid | 2.50 |
| 46 | 3-methoxy-4-methylbenzoic acid | 2.10 |
| 47 | 4-phenylbutyric acid | 3.00 |
| 48 | 4-butylbenzoic acid | 2.60 |
| 49 | 3,5-dimethylbenzoic acid | 1.94 |
| 50 | 3,5-bis(trifluoromethyl)-benzoic acid | 0.96 |
| 51 | 3,4-dimethoxybenzoic acid | 3.08 |
| 52 | 4-ethyl-4-biphenylcarboxylic acid | 0.92 |
| 53 | 3,4,5-trimethoxybenzoic acid | 1.46 |
| 54 | 3,4,5-triethoxybenzoic acid | 2.37 |
| 55 | butyric acid | 3.39 |
| 56 | heptanoic acid | 3.51 |
| 57 | isobutyric acid | 3.11 |
| 58 | (+/−)-2-methylbutyric acid | 6.25 |
| 59 | isovaleric acid | 6.36 |
| 60 | 3-methylvaleric acid | 5.06 |
| 61 | 4-methylvaleric acid | 3.32 |
| 62 | crotonic acid | 5.26 |
| 63 | vinylacetic acid | 1.30 |
| 64 | 2-ethyl-2-hexenoic acid | 11.63 |
| 65 | p-toluic acid | 2.28 |
| 66 | p-anisic acid | 5.38 |
| 67 | trimethylacetic acid | 4.24 |
| 68 | cyclohexanecarboxylic acid | 3.51 |
| 69 | cyclohexylacetic acid | 3.95 |
| 70 | cyclohexanebutyric acid | 3.33 |
| 71 | cycloheptanecarboxylic acid | 2.60 |
| 72 | acetic acid | 2.65 |
| 73 | 2-methylcyclopropanecarboxylic acid | 2.42 |
| 74 | cyclobutanecarboxylic acid | 2.77 |
| 75 | cyclopentanecarboxylic acid | 3.03 |
| 76 | 3-cyclopentylpropionic acid | 3.71 |
| 77 | 2-furoic acid | 4.44 |
| 78 | cyclohexanepropionic acid | 2.80 |
| 79 | 4-methyl-1-cyclohexanecarboxylic acid | 5.92 |
| 80 | 4-tert-butyl-cyclohexanecarboxylic acid | 6.64 |
| 81 | 4-methylcyclohexaneacetic acid | 4.79 |
| 82 | tiglic acid | 4.59 |
| 83 | 2-norbornaneacetic acid | 5.45 |
| 84 | 1-adamantaneacetic acid | 11.16 |
| 85 | 2-thiophenecarboxylic acid | 1.16 |

TABLE 3

Amino Acid Ratios

| No. | AA | ratio |
|---|---|---|
| 1 | Boc-L-Ala | 0.95 |
| 2 | Boc-L-Phe | 0.81 |
| 3 | Boc—Gly | 1.00 |
| 4 | Boc-L-His(Dnp) | 0.85 |
| 5 | Box-L-Lys(Cbz) | 1.05 |
| 6 | Boc-L-Met(O) | 0.89 |
| 7 | Boc-L-Gln | 1.20 |
| 8 | Boc-L-Tyr(Brz) | 1.26 |
| 9 | Boc-L-α-aminobutyric acid | 0.94 |
| 10 | Boc-L-Nve | 1.15 |
| 11 | Boc-L-Nle | 1.15 |
| 12 | Boc-L-Orn(Cbz) | 1.06 |
| 13 | Boc-L-Phg | 0.66 |
| 14 | Boc-L-Nap | 0.55 |
| 15 | Boc-L-Cha | 1.50 |
| 16 | Boc-L-Met—$O_2$ | 0.90 |
| 17 | Boc-L-p-$NO_2$—Phe | 1.00 |
| 18 | Boc-L-p-Cl—Phe | 1.00 |
| 19 | Boc-L-F—Phe | 1.00 |
| 20 | Boc-L-(3-pyridyl)-Ala | 1.00 |
| 21 | Boc-L-(2-thienyl)-Ala | 1.00 |
| 22 | Boc-L-tBu—Gly | 2.00 |
| 23 | Boc-L-Tic | 1.00 |
| 24 | Boc-L-homoPro | 1.00 |
| 25 | Boc-O-Ethyl-Tyr | 1.20 |

EXAMPLE I

This example provides the solid-phase combinatorial synthesis of a library containing a mixture of approximately 46,750 imidazol-pyrido-indole and imidazol-pyrido-benzothiophene derivatives.

The $R^1$, $R^2$ and $R^3$ groups varied as described above and below. Again, two β-(3-benzothienyl)Ala and eleven Trp amino acid derivatives were used in the synthesis, and in the two instances, individual D and L derivatives were ultimately pooled as DL mixtures, for a total of eleven different $R^1$ groups. The Trp and Ala amino acids used to generate $R^1$ are again listed in Table 4. Twenty-five second amino acids were used to generate the various $R^2$ groups, also summarized again in Table 4. All amino acids were Boc-protected and side chain protection used is shown in the table below. Finally, eighty-five carboxylic acids, as summarized in Table 4, were used to acylate the dipeptides to generate the $R^3$ variability. Therefore, Table 4 provides a summary of all the amino acids ($R^1$ and $R^2$) and carboxylic acid components ($R^3$) used in the preparation of the library.

TABLE 4

SUMMARY OF R GROUPS IN PREPARED LIBRARIES

| No. | R¹ | R² | R³ |
|---|---|---|---|
| 1 | β-(3-benzothienyl)-Ala | Ala | 1-phenyl-1-cyclopropanecarboxylic acid |
| 2 | β-(3-benzothienyl)-D-Ala | Phe | 2-phenylbutyric acid |
| 3 | 6-fluoro-DL-Trp | Gly | 3-phenylbutyric acid |
| 4 | 5-fluoro-DL-Trp | His(Dnp) | m-tolylacetic acid |
| 5 | 5-bromo-DL-Trp | Lys(Cbz) | 3-fluorophenylacetic acid |
| 6 | 5-hydroxy-DL-Trp | Met(O) | 3-bromophenylacetic acid |
| 7 | 1-methyl-DL-Trp | Gln | (α,α,α-trifluoro-m-tolyl)acetic acid |
| 8 | 5-methyl-DL-Trp hydrate | Tyr(Brz) | p-tolylacetic acid |
| 9 | N-α-methyl-DL-Trp | α-Aba | 4-fluorophenylacetic acid |
| 10 | 6-methyl-DL-Trp | Nve | 3-methoxyphenylacetic acid |
| 11 | 7-methyl-DL-Trp | Nle | 4-bromophenylacetic acid |
| 12 | Trp | Orn(Cbz) | 4-methoxyphenylacetic acid |
| 13 | D-Trp | Phg | 4-ethoxyphenylacetic acid |
| 14 | | Nap | 4-isobutyl-α-methylphenylacetic acid |
| 15 | | Cha | 3,4-dichlorophenylacetic acid |
| 16 | | Met—O₂ | 3,5-bis(trifluoromethyl)phenylacetic acid |
| 17 | | pNO₂—Phe | 3-(3,4-dimethoxyphenyl)-propionic acid |
| 18 | | pCl—Phe | 4-biphenylacetic acid |
| 19 | | pF—Phe | α-methylcinnamic acid |
| 20 | | 3-pyridyl-Ala | 2-(trifluoromethyl)-cinnamic acid |
| 21 | | 2-thienyl-Ala | (3,4-dimethoxyphenyl)-acetic acid |
| 22 | | t-Bu—Gly | 3,4-(methylenedioxy)-phenylacetic acid |
| 23 | | Tic | 2-methoxycinnamic acid |
| 24 | | homoPro | 3,4-(methylenedioxy)-cinnamic acid |
| 25 | | O—Et—Tyr | 2-hydroxycinnamic acid |
| 26 | | | benzoic acid |
| 27 | | | 4-chlorocinnamic acid |
| 28 | | | m-anisic acid |
| 29 | | | 4-isopropylbenzoic acid |
| 30 | | | 4-vinylbenzoic acid |
| 31 | | | 4-fluorobenzoic acid |
| 32 | | | 4-bromobenzoic acid |
| 33 | | | 3,4-dimethoxycinnamic acid |
| 34 | | | 4-hydroxybenzoic acid |
| 35 | | | trans-cinnamic acid |
| 36 | | | 3,4-dimethylbenzoic acid |
| 37 | | | 3-fluoro-4-methylbenzoic acid |
| 38 | | | 3-bromo-4-methylbenzoic acid |
| 39 | | | 3-iodo-4-methylbenzoic acid |
| 40 | | | 3,4-dichlorobenzoic acid |
| 41 | | | 4-biphenylcarboxylic acid |
| 42 | | | 3,4-diflurobenzoic acid |
| 43 | | | m-toluic acid |
| 44 | | | phenylacetic acid |
| 45 | | | hydrocinnamic acid |
| 46 | | | 3-methoxy-4-methylbenzoic acid |
| 47 | | | 4-phenylbutyric acid |
| 48 | | | 4-butylbenzoic acid |
| 49 | | | 3,5-dimethylbenzoic acid |
| 50 | | | 3,5-bis(trifluoromethyl)-benzoic acid |
| 51 | | | 3,4-dimethoxybenzoic acid |
| 52 | | | 4-ethyl-4-biphenyl-carboxylic acid |
| 53 | | | 3,4,5-trimethoxybenzoic acid |
| 54 | | | 3,4,5-triethoxybenzoic acid |
| 55 | | | butyric acid |
| 56 | | | heptanoic acid |
| 57 | | | isobutyric acid |
| 58 | | | (+/−)-2-methylbutyric acid |
| 59 | | | isovaleric acid |
| 60 | | | 3-methylvaleric acid |
| 61 | | | 4-methylvaleric acid |
| 62 | | | crotonic acid |
| 63 | | | vinylacetic acid |
| 64 | | | 2-ethyl-2-hexenoic acid |
| 65 | | | p-toluic acid |
| 66 | | | p-anisic acid |
| 67 | | | trimethylacetic acid |
| 68 | | | cyclohexanecarboxylic acid |
| 69 | | | cyclohexylacetic acid |
| 70 | | | cyclohexanebutyric acid |
| 71 | | | cycloheptanecarboxylic acid |
| 72 | | | acetic acid |
| 73 | | | 2-methylcyclopropane-carboxylic acid |
| 74 | | | cyclobutanecarboxylic acid |
| 75 | | | cyclopentanecarboxylic acid |
| 76 | | | 3-cyclopentylpropionic acid |
| 77 | | | 2-furioc acid |
| 78 | | | cyclohexanepropionic acid |
| 79 | | | 4-methyl-1-cyclohexanecarboxylic acid |
| 80 | | | 4-tert-butyl-cyclohexanecarboxylic acid |
| 81 | | | 4-methylcyclohexaneacetic acid |
| 82 | | | tiglic acid |
| 83 | | | 2-norbornaneacetic acid |
| 84 | | | 1-adamantaneacetic acid |
| 85 | | | 2-thiophenecarboxylic acid |

The library was synthesized in the positional scanning format of XXO, XOX, and OXX in which one position was defined while the other two positions were mixtures. The library was synthesized using the "tea-bag" synthesis approach, as described in U.S. Pat. No. 4,631,211 and R. Houghten, *Proc. Natl. Acad. Sci.*, 82:5135 (1985), where aliquots of a polystyrene resin are contained within polypropylene mesh to allow for common procedures to be done simultaneously. Mixture position R¹ was obtained by the "divide, couple, and recombine" procedure, also known as the "split resin" method, as described in Houghten et al., *Nature*, 354:84 (1991). Mixture positions $R^2$ and $R^3$ were done using the "chemical mixture" approach, as described in Ostresh et al., *Biopolymers*, 34: 1681 (1994), where all the reactants in that position, were combined according to predetermined ratios in one vessel and then allowed to react. Boc protected amino acids and unprotected carboxylic acids were coupled to p-methylbenzyhdrylamine derivatized polystyrene resin using solid phase peptide synthesis procedures.

Specifically, the synthesis was as follows. The synthesis which follows is with reference to the Trp derivatives. It should be appreciated, however, that the same procedures can be, and were, used for the Ala derivatives as well.

A. Boc Protection of Trp:

For 1 equivalent of free amine to be Boc protected, 1.5 eq of di-tert-butyl dicarbonate ($Boc_2O$), and 1.2 eq of diisopropylethylamine (DIEA) were used. The $Boc_2O$ was dissolved in 1,4-dioxane at a 1M concentration and the amino acid was at a 1M concentration in $H_2O$.

A representative Boc protection with 6-fluoro-DL-Trp was as follows. The 6-fluoro-DL-Trp (4 g) was dissolved in 18 ml of $H_2O$, then 3.8 ml of DIEA were added. In a separate vial 5.893 g of $Boc_2O$ was dissolved in 27 ml of 1,4-dioxane. The two solutions were combined in a 250 ml round bottom flask along with a teflon coated stir bar. The reaction ran overnight (~18 hours) at room temperature with continuous stirring. The same amount of $Boc_2O$ was added again after the ~18 hours and was allowed to react an additional 4 hours. The solution was then transferred to a lyophilizer flask, shell frozen, and lyophilized. Once dry, the amino acid was resuspended in 15 ml of $H_2O$ and 15 ml of 1N $NaOH/H_2O$. The basic $H_2O$ layer was transferred to a separatory funnel and washed (4×15 ml) with ethyl acetate (EtOAc). The EtOAc washes were combined and set aside. The basic $H_2O$ layer was transferred to a 500 ml round bottom flask along with a teflon coated stir bar. The water layer was then acidified to a pH of 2–3 with 0.5M $HCl/H_2O$. Once acidified, the water layer was transferred back into the separatory funnel and extracted (4×20 ml) with EtOAc. The EtOAc extractions were combined, dried with $MgSO_4$, filtered, and then stripped down using a rotovap. The Boc protected amino acid was dissolved in 100% acetonitrile and then diluted to a 50% acetonitrile/$H_2O$ concentration, frozen and lyophilized. Boc protection of amino acid was monitored and purity was confirmed by thin-layer chromatography.

B. Boc-Protected Trp Coupling to Resin:

A total of 1.5 g of p-methylbenzhydrylamine (mBHA) resin (0.81 meq/g, 100–200 mesh) was contained within a 3.5"×3.5" polypropylene mesh "tea-bag" (McMaster Carr, Chicago, Ill.). Reactions were carried out in 125 ml polyethylene bottles. Following neutralization of the resin with 5% diisopropylethylamine (DIEA) in Dichloromethane (DCM) (3×60 ml), the resin was washed with DCM (2×60 ml). A 6X excess of the Boc Trp derivative, to the amine, was weighed into the polyethylene bottle. Hydroxybenzotriazole (HOBt; 36.5 ml of 0.2M) in dimethyformamide (DMF) and 36.5 ml of 0.2M diisopropylcarbodiimide (DIC) in DMF were added. The final coupling concentration of the amino acid was 0.1M. The reaction was allowed to go overnight (19 hours) on a reciprocating shaker. Resin was washed with DMF (2×60 ml), DCM (2×60 ml), and methanol (1×60 ml). Bags were allowed to air dry.

For mixture position $R^1$, equal equivalents of each of the Trp derivative resins were combined in a pyrex dish and suspended in a sufficient amount of DMF for adequate mixing. The resins were allowed to rapidly stir for 45 minutes. Resin mixture was transferred to a large polypropylene mesh bag and washed with DCM (2×1L) and methanol (1×1L). The bag was allowed to air dry. New substitution was equal to 0.65 meq/g.

One hundred mg of either the defined Boc Trp derivative resin or 100 mg of the Boc Trp mixture resin was weighed into 1.51"×1.5" polypropylene mesh bags. The Boc protecting group was removed by a 30 minute treatment of 55% trifluoroacetic acid (TFA) in DCM (15 ml). The resin was then washed with DCM (1×15 ml), IPA (2×15 ml) , and DCM (2×15 ml).

C. Second Amino Acid Coupling:

Following neutralization of the Trp derivative resin with 5% DIEA in DCM (3×15 ml), the resin was washed with DCM (2×15 ml). Each amino acid (6X) was weighed into a 30 ml polyethylene bottle and 3.9 ml of 0.2M HOBt in DMF and 3.9 ml of 0.2M DIC in DMF were added to each. The final coupling concentration was 0.1M. The reaction was allowed to go overnight (14 hours) on a reciprocating shaker. The resin was then washed with DMF (1×15 ml) and with DCM (1×15 ml).

For mixture position $R^2$, all amino acids were combined, in a 500 ml polyethylene bottle, according to predetermined ratios as set forth above in the Introduction with the minimum being a 6X excess over the amine. To the bottle was added 80.5 ml of DMF and 80.5 ml 0.5M DIC in DMF along with 6.158 g of HOBt (1 eq HOBt: 1 eq amino acid). Amounts were based on 103×100 mg bags. The final coupling concentration was 0.25M. The reaction was allowed to go overnight (14 hours) on a reciprocating shaker. The resin was then washed with DMF (1×15 ml) and with DCM (1×15 ml).

The Boc protecting group for the defined and mixture resins was removed by a 30 minute treatment of 55% TFA in DCM (15 ml). The resin was then washed with DCM (1×15 ml), IPA (2×15 ml), and DCM (2×15 ml).

D. Carboxylic Acid Coupling:

Following neutralization of the resin with 5% DIEA in DCM (3×15 ml), the resin was washed with DCM (2×15 ml). Each carboxylic acid (10X) was either weighed or pipetted into a 30 ml polyethylene bottle. To each were added 6.6 ml of 0.2M HOBt in DMF and 6.6 ml of 0.2M DIC in DMF. The final coupling concentration was 0.1M. The reaction was allowed to go overnight (16 hours) on a reciprocating shaker. The resin was then washed with DMF (2×15 ml) and with DCM (2×15 ml).

For mixture position $R^3$, all carboxylic acids were combined, in a 1L polyethylene bottle, according to predetermined ratios as set forth above in the Introduction with the minimum being a 10X excess over the amine. To the bottle 355 ml of 0.5M HOBt in DMF and 355 ml of 0.5M DIC in DMF were added. The amounts were based on 36×100 mg bags. The final coupling concentration was 0.25M. The reaction was allowed to go overnight (16 hours) on a reciprocating shaker. The resin was then washed with DMF (2×15 ml) and with DCM (2×15 ml).

E. Dinitrophenyl Deprotection (DNP Removal):

The dinitrophenyl was removed from histidine by shaking the resin containing bags in a solution of 97.5% DMF/2.5% thiophenol (5 ml, 1 hour), followed by washes of DMF (3×15 ml), and alternating IPA and DCM washes (12 each× 15 ml).

F. Boc Amino Acid Side-Chain Protecting Group Removal:

Using low hydrogen fluoride (HF) procedure, the side-chain protecting groups were removed by shaking the resin containing bags in a solution of 60% dimethylsulfide/5% ethanedithiol/10% p-Cresol/25% HF (5 ml, 2 hours at 0° C.). The resin was then alternatingly washed with IPA and DCM (8 each×15 ml), DMF (4×15 ml), DCM (3×15 ml), and methanol (1×15 ml).

G. Condensation (Ring Closure):

In a glove box under nitrogen atmosphere, resin was rinsed with anhydrous 1,4-dioxane and then placed in a 50 ml Kimax tube. 16.5 ml of 0.1M phosphorous oxychloride in anhydrous 1,4-dioxane (25X) was added to the tube. The tube was capped tightly and removed from the glove box. Resin was heated overnight (18 hours) at 85° C. in a heated silicone oil bath. Resin was removed from heat and allowed to cool to room temperature. Resin was then washed with 1,4-dioxane (1×20 ml), followed by alternating washes of DMF and methanol (3 each×20 ml). The resin was air dried.

H. HF Cleavage:

The resin was cleaved with 92.5% HF/7.5% anisole (5 ml, 1.5 hours at 0° C.), followed by extraction and lyophilization of product.

EXAMPLE II

Following the procedures of Example I, the following pools of libraries containing imidazol-pyrido-indole and imidazol-pyrido-benzothiophene derivatives were prepared by the positional scan format. The pool reference numbers are identified in Table 5 below. Based on the positional scan format, "X" means a mixture of all possible substituents at that position.

As described above, the β-(3-benzothienyl)-L-Ala and β-(3-benzothienyl)-D-Ala were combined for a mixture at the $R^1$ position of β-(3-benzothienyl)-DL-Ala. Similarly, the L-Trp and D-Trp derivatives were combined for DL-Trp.

Each of the 121 pools were screened in an anti-microbial assay and μ-opioid receptor assay as provided in Example III. This example and Table 5 is provided for further reference for pool compositions in relation to the biological data in the ensuing Example.

TABLE 5

LIBRARY POOL REFERENCE NUMBERS AND VARIABLE R GROUPS FOR Imidazol-pyrido-indole LIBRARY

| Pool No. | $R^1$ | $R^2$ | $R^3$ |
|---|---|---|---|
| 1 | β-(3-benzo-thienyl)-DL-Ala | X | X |
| 2 | 6-fluoro-DL-Trp | X | X |
| 3 | 5-fluoro-DL-Trp | X | X |
| 4 | 5-bromo-DL-Trp | X | X |
| 5 | 5-hydroxy-DL-Trp | X | X |
| 6 | 1-methyl-DL-Trp | X | X |
| 7 | 5-methyl-DL-Trp hydrate | X | X |
| 8 | N-α-methyl-DL-Trp | X | X |
| 9 | 6-methyl-DL-Trp | X | X |
| 10 | 7-methyl-DL-Trp | X | X |
| 11 | DL-Trp | X | X |
| 12 | X | Ala | X |
| 13 | X | Phe | X |
| 14 | X | Gly | X |
| 15 | X | His | X |
| 16 | X | Lys | X |

TABLE 5-continued

LIBRARY POOL REFERENCE NUMBERS AND VARIABLE R GROUPS FOR Imidazol-pyrido-indole LIBRARY

| Pool No. | $R^1$ | $R^2$ | $R^3$ |
|---|---|---|---|
| 17 | X | Met(O) | X |
| 18 | X | Gln | X |
| 19 | X | Tyr | X |
| 20 | X | α-Aba | X |
| 21 | X | Nve | X |
| 22 | X | Nle | X |
| 23 | X | Orn | X |
| 24 | X | Phg | X |
| 25 | X | Nap | X |
| 26 | X | Cha | X |
| 27 | X | Met—$O_2$ | X |
| 28 | X | $pNO_2$—Phe | X |
| 29 | X | pCl—Phe | X |
| 30 | X | pF—Phe | X |
| 31 | X | 3-pyridyl-Ala | X |
| 32 | X | 2-thienyl-Ala | X |
| 33 | X | t-Bu—Gly | X |
| 34 | X | Tic | X |
| 35 | X | homoPro | X |
| 36 | X | O—Et—Tyr | X |
| 37 | X | X | 1-phenyl-1-cyclopropane-carboxylic acid |
| 38 | X | X | 2-phenylbutyric acid |
| 39 | X | X | 3-phenylbutyric acid |
| 40 | X | X | m-tolylacetic acid |
| 41 | X | X | 3-fluorophenylacetic acid |
| 42 | X | X | 3-bromophenylacetic acid |
| 43 | X | X | (α,α,α-trifluoro-m-tolyl) acetic acid |
| 44 | X | X | p-tolylacetic acid |
| 45 | X | X | 4-fluorophenylacetic acid |
| 46 | X | X | 3-methoxyphenylacetic acid |
| 47 | X | X | 4-bromophenylacetic acid |
| 48 | X | X | 4-methoxyphenylacetic acid |
| 49 | X | X | 4-ethoxyphenylacetic acid |
| 50 | X | X | 4-isobutyl-α-methylphenylacetic acid |
| 51 | X | X | 3,4-dichlorophenylacetic acid |
| 52 | X | X | 3,5-bis(trifluoromethyl) phenylacetic acid |
| 53 | X | X | 3-(3,4-dimethoxyphenyl)-propionic acid |
| 54 | X | X | 4-biphenylacetic acid |
| 55 | X | X | α-methylcinnamic acid |
| 56 | X | X | 2-(trifluoromethyl)cinnamic acid |
| 57 | X | X | (3,4-dimethoxyphenyl)acetic acid |
| 58 | X | X | 3,4-(methylenedioxy)-phenylacetic acid |
| 59 | X | X | 2-methoxycinnamic acid |
| 60 | X | X | 3,4-(methylenedioxy)-cinnamic acid |
| 61 | X | X | 2-hydroxycinnamic acid |
| 62 | X | X | benzoic acid |
| 63 | X | X | 4-chlorocinnamic acid |
| 64 | X | X | m-anisic acid |
| 65 | X | X | 4-isopropylbenzoic acid |
| 66 | X | X | 4-vinylbenzoic acid |
| 67 | X | X | 4-fluorobenzoic acid |
| 68 | X | X | 4-bromobenzoic acid |
| 69 | X | X | 3,4-dimethoxycinnamic acid |
| 70 | X | X | 4-hydroxybenzoic acid |

TABLE 5-continued

LIBRARY POOL REFERENCE NUMBERS AND VARIABLE R GROUPS FOR Imidazol-pyrido-indole LIBRARY

| Pool No. | $R^1$ | $R^2$ | $R^3$ |
|---|---|---|---|
| 71 | X | X | trans-cinnamic acid |
| 72 | X | X | 3,4-dimethylbenzoic acid |
| 73 | X | X | 3-fluoro-4-methylbenzoic acid |
| 74 | X | X | 3-bromo-4-methylbenzoic acid |
| 75 | X | X | 3-iodo-4-methylbenzoic acid |
| 76 | X | X | 3,4-dichlorobenzoic acid |
| 77 | X | X | 4-biphenylcarboxylic acid |
| 78 | X | X | 3,4-difluorobenzoic acid |
| 79 | X | X | m-toluic acid |
| 80 | X | X | phenylacetic acid |
| 81 | X | X | hydrocinnamic acid |
| 82 | X | X | 3-methoxy-4-methylbenzoic acid |
| 83 | X | X | 4-phenylbutyric acid |
| 84 | X | X | 4-butylbenzoic acid |
| 85 | X | X | 3,5-dimethylbenzoic acid |
| 86 | X | X | 3,5-bis(trifluoromethyl)-benzoic acid |
| 87 | X | X | 3,4-dimethoxybenzoic acid |
| 88 | X | X | 4-ethyl-4-biphenyl-carboxylic acid |
| 89 | X | X | 3,4,5-trimethoxybenzoic acid |
| 90 | X | X | 3,4,5-triethoxybenzoic acid |
| 91 | X | X | butyric acid |
| 92 | X | X | heptanoic acid |
| 93 | X | X | isobutyric acid |
| 94 | X | X | (+/−)-2-methylbutyric acid |
| 95 | X | X | isovaleric acid |
| 96 | X | X | 3-methylvaleric acid |
| 97 | X | X | 4-methylvaleric acid |
| 98 | X | X | crotonic acid |
| 99 | X | X | vinylacetic acid |
| 100 | X | X | 2-ethyl-2-hexenoic acid |
| 101 | X | X | p-toluic acid |
| 102 | X | X | p-anisic acid |
| 103 | X | X | trimethylacetic acid |
| 104 | X | X | cyclohexanecarboxylic acid |
| 105 | X | X | cyclohexylacetic acid |
| 106 | X | X | cyclohexanebutyric acid |
| 107 | X | X | cycloheptanecarboxylic acid |
| 108 | X | X | acetic acid |
| 109 | X | X | 2-methylcyclopropane-carboxylic acid |
| 110 | X | X | cyclobutanecarboxylic acid |
| 111 | X | X | cyclopentanecarboxylic acid |
| 112 | X | X | 3-cyclopentylpropionic acid |
| 113 | X | X | 2-furoic acid |
| 114 | X | X | cyclohexanepropionic acid |
| 115 | X | X | 4-methyl-1-cyclohexanecarboxylic acid |
| 116 | X | X | 4-tert-butyl-cyclohexanecarboxylic acid |
| 117 | X | X | 4-methylcyclohexaneacetic acid |
| 118 | X | X | tiglic acid |
| 119 | X | X | 2-norbornaneacetic acid |
| 120 | X | X | 1-adamantaneacetic acid |
| 121 | X | X | 2-thiophenecarboxylic acid |

EXAMPLE III

This example describes initial biological screens of all 121 library pools as identified in the above Example II. More specifically, this example provides an initial screen of all the imidazol-pyrido-indoles and imidazol-pyrido-benzothiophenes in (1) the anti-microbial assay and (2) the $\mu$-opioid receptor assay, each of which are described in detail above. The results of those screens are provided in Table 6 below. In addition, the results of the $\mu$-opioid receptor assay are depicted graphically in FIGS. 1 and 2. Specifically, FIG. 1a graphically depicts the $\mu$-opioid receptor assay data for pools 1 to 11, having the $R^1$ position constant and $R^2$ and $R^3$ variable in each of the eleven pools. FIG. 1b provides the data for pools 12 to 37, varying at $R^1$ and $R^3$ and having $R^2$ constant as provided in Table 6. Finally, FIG. 2 graphically represents the results of the screen for pools 38 to 121, with $R^1$ and $R^2$ variable and $R^3$ constant in each of those pools.

The results of these assays evidence that many of the compounds contained within the libraries are biologically active, either as an anti-microbial or an inhibitor of a specific opioid receptor.

TABLE 6

Assays Of The Imidazol-pyrido-indole Library (Positional Scanning Format)

| No. | Anti-Microbial Assay ($IC_{50}$, $\mu$g/ml) | $\mu$-Opioid Receptor Assay (% Bound) |
|---|---|---|
| 1 | 165.40 | 32 |
| 2 | 16.56 | 6 |
| 3 | 16.19 | 12 |
| 4 | 11.98 | 9 |
| 5 | 29.43 | 10 |
| 6 | 45.24 | 12 |
| 7 | 19.49 | 16 |
| 8 | 24.16 | 15 |
| 9 | 17.99 | 22 |
| 10 | 17.25 | 18 |
| 11 | 22.42 | 13 |
| 12 | 44.65 | 18 |
| 13 | 51.87 | 28 |
| 14 | 21.03 | 20 |
| 15 | 13.17 | 12 |
| 16 | 10.22 | 8 |
| 17 | 17.27 | 6 |
| 18 | 22.14 | 10 |
| 19 | 23.73 | 16 |
| 20 | 21.39 | 14 |
| 21 | 16.78 | 11 |
| 22 | 24.31 | 24 |
| 23 | 7.77 | 6 |
| 24 | 21.17 | 36 |
| 25 | 21.09 | 32 |
| 26 | 12.57 | 42 |
| 27 | 171.05 | 23 |
| 28 | 67.37 | 23 |
| 29 | 18.92 | 34 |
| 30 | 22.83 | 29 |
| 31 | 59.69 | 12 |
| 32 | 86.86 | 31 |
| 33 | 12.72 | 26 |
| 34 | 9.13 | 1 |
| 35 | 15.92 | 11 |
| 36 | 115.20 | 27 |
| 37 | 25.03 | 14 |
| 38 | 70.68 | 20 |
| 39 | 16.60 | 12 |
| 40 | 16.79 | 14 |
| 41 | 19.21 | 8 |
| 42 | 17.38 | 7 |

TABLE 6-continued

Assays Of The Imidazol-pyrido-indole Library (Positional Scanning Format)

| No. | Anti-Microbial Assay (IC$_{50}$, µg/ml) | µ-Opioid Receptor Assay (% Bound) |
| --- | --- | --- |
| 43 | 15.02 | 13 |
| 44 | 17.70 | 13 |
| 45 | 22.37 | 9 |
| 46 | 27.81 | 8 |
| 47 | 13.41 | 10 |
| 48 | 46.33 | 15 |
| 49 | 26.35 | 10 |
| 50 | 18.90 | 22 |
| 51 | 10.68 | 11 |
| 52 | 12.85 | 19 |
| 53 | 84.26 | 0 |
| 54 | 15.74 | 23 |
| 55 | 18.63 | 5 |
| 56 | 13.82 | 8 |
| 57 | 128.79 | 9 |
| 58 | 12.97 | 25 |
| 59 | 40.37 | 3 |
| 60 | 8.48 | 5 |
| 61 | 11.00 | 0 |
| 62 | 26.30 | 7 |
| 63 | 18.02 | 2 |
| 64 | 31.90 | 7 |
| 65 | 30.39 | 12 |
| 66 | 23.29 | 12 |
| 67 | 26.21 | 11 |
| 68 | 28.67 | 8 |
| 69 | 55.48 | 2 |
| 70 | 9.02 | 0 |
| 71 | 23.65 | 0 |
| 72 | 19.49 | 11 |
| 73 | 22.07 | 7 |
| 74 | 15.17 | 13 |
| 75 | 19.98 | 16 |
| 76 | 24.46 | 12 |
| 77 | 26.80 | 22 |
| 78 | 45.76 | 23 |
| 79 | 40.37 | 15 |
| 80 | 20.13 | 11 |
| 81 | 14.46 | 6 |
| 82 | 22.18 | 9 |
| 83 | 15.69 | 5 |
| 84 | 26.90 | 30 |
| 85 | 18.75 | 17 |
| 86 | 35.58 | 39 |
| 87 | 29.92 | 15 |
| 88 | 29.19 | 52 |
| 89 | 55.43 | 10 |
| 90 | 45.09 | 19 |
| 91 | 19.96 | 6 |
| 92 | 22.58 | 9 |
| 93 | 25.23 | 8 |
| 94 | 55.41 | 15 |
| 95 | 17.52 | 4 |
| 96 | 18.93 | 8 |
| 97 | 17.74 | 5 |
| 98 | 23.80 | 4 |
| 99 | 26.66 | 5 |
| 100 | 23.90 | 13 |
| 101 | 18.20 | 17 |
| 102 | 21.78 | 11 |
| 103 | 27.59 | 17 |
| 104 | 20.27 | 20 |
| 105 | 16.77 | 13 |
| 106 | 16.48 | 21 |
| 107 | 43.56 | 12 |
| 108 | 29.87 | 13 |
| 109 | 22.86 | 10 |
| 110 | 29.53 | 10 |
| 111 | 30.88 | 11 |
| 112 | 31.06 | 11 |
| 113 | 75.08 | 8 |
| 114 | 18.66 | 8 |
| 115 | 12.93 | 17 |
| 116 | 14.99 | 16 |
| 117 | 14.81 | 16 |
| 118 | 42.25 | 11 |
| 119 | 12.65 | 10 |
| 120 | 9.01 | 25 |
| 121 | 55.07 | 11 |

All journal article and reference citations provided above, in parentheses or otherwise, whether previously stated or not, are incorporated herein by reference.

Although the invention has been described with reference to the examples provided above, it should be understood that various modifications can be made without departing from the spirit of the inventions. Accordingly the invention is limited only by the claims.

We claim:

1. A library of two or more imidazole compounds comprising the structure:

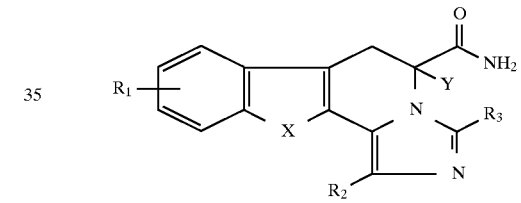

wherein

R$^1$ is selected from the group consisting of a hydrogen atom, halo, hydroxy, protected hydroxy, C$_1$ to C$_{10}$ alkyl, C$_1$ to C$_{10}$ substituted alkyl, amino, carboxy, and protected carboxy;

R$^2$ is selected from the group consisting of a hydrogen atom, C$_1$ to C$_{10}$ alkyl, C$_1$ to C$_{10}$ substituted alkyl, phenyl, substituted phenyl, C$_7$ to C$_{16}$ phenylalkyl, C$_7$ to C$_{16}$ substituted phenylalkyl, C$_3$ to C$_7$ cycloalkyl, C$_3$ to C$_7$ substituted cycloalkyl, benzyl, substituted benzyl, naphthyl, substituted naphthyl, and when taken in conjunction with C1 and N2 to form a piperidine or benzopiperidine;

R$^3$ is selected from the group consisting of C$_1$ to C$_{10}$ alkyl, C$_1$ to C$_{10}$ substituted alkyl, C$_2$ to C$_{10}$ alkenyl, C$_2$ to C$_{10}$ substituted alkenyl, C$_3$ to C$_7$ cycloalkyl, C$_3$ to C$_7$ substituted cycloalkyl, phenyl, substituted phenyl, C$_7$ to C$_{16}$ phenylalkyl, C$_7$ to C$_{16}$ substituted phenylalkyl, C$_7$ to C$_{16}$ phenylalkenyl, C$_7$ to C$_{16}$ substituted phenylalkenyl, benzyl, substituted benzyl, naphthyl, substituted naphthyl, heterocycle, and substituted heterocycle;

X is selected from the group consisting of a nitrogen atom (N) and a sulfur atom (S); and Y is selected from the group consisting of a hydrogen atom and methyl.

2. The library of claim 1, wherein:
R¹ is selected from the group consisting of a hydrogen atom, halo, hydroxy, and $C_1$ to $C_{10}$ alkyl;
R² is selected from the group consisting of a hydrogen atom, $C_1$ to $C_{10}$ alkyl, $C_1$ to $C_{10}$ substituted alkyl, phenyl, $C_3$ to $C_7$ substituted cycloalkyl, benzyl, substituted benzyl, substituted naphthyl, and when taken in conjunction with C1 and N2 to form a piperidine or benzopiperidine;
R³ is selected from the group consisting of $C_1$ to $C_{10}$ alkyl, $C_1$ to $C_{10}$ substituted alkyl, $C_2$ to $C_{10}$ alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, $C_7$ to $C_{16}$ phenylalkenyl, $C_7$ to $C_{16}$ substituted phenylalkenyl, and heterocycle;
X is selected from the group consisting of a nitrogen atom and a sulfur atom; and
Y is selected from the group consisting of a hydrogen atom and methyl.

3. The library of claim 1, wherein:
R¹ is selected from the group consisting of a hydrogen atom, fluoro, bromo, hydroxy, and methyl;
R² is selected from the group consisting of methyl, benzyl, a hydrogen atom, 3-imidazoylmethyl, aminobutyl, methylsulfinylethyl, carbamoylethyl, 4-hydroxybenzyl, ethyl, propyl, butyl, aminopropyl, phenyl, naphthylmethyl, cyclohexylmethyl, methylsulfonylethyl, 4-nitrobenzyl, 4-chlorobenzyl, 4-fluorobenzyl, 3-pyridylmethyl, 2-thienylmethyl, 1-butyl, 4-ethoxybenzyl, and when taken in conjunction with C1 and N2 to form a piperidine or benzopiperidine;
R³ is selected from the group consisting of 1-phenylcyclopropyl, 1-phenylproply, 2-phenylpropyl, 3-methylbenzyl, 3-fluorobenzyl, 3-bromobenzyl, 3-trifluoromethylbenzyl, 4-methylbenzyl, 4-fluorobenzyl, 3-methoxybenzyl, 4-bromobenzyl, 4-methoxybenzyl, 4-ethoxybenzyl, 4-isobutylphenethyl, 3,4-dichlorobenzyl, 3,5-bis(trifluoromethyl)-benzyl, 3,4-dimethoxyphenethyl, 4-phenylbenzyl, α-methylstyryl, 2-trifluoromethylstyryl, 3,4-dimethoxybenzyl, 3,4-dihydroxybenzyl, 2-methoxystyryl, 3,4-dihydroxystyryl, 2-hydroxystyryl, phenyl, 4-chlorostyryl, m-anisyl, 4-isopropylphenyl, 4-vinylphenyl, 4-fluorophenyl, 4-bromophenyl, 3,4-dimethoxystyryl, 4-hydroxyphenyl, styryl, 3,4-dimethylphenyl, 3-fluoro-4-methylphenyl, 3-bromo-4-methylphenyl, 3-iodo-4-methylphenyl, 3,4-dichlorophenyl, 4-biphenyl, 3,4-difluorophenyl, m-tolyl, benzyl, phenethyl, 3-methoxy-4-methylphenyl, 3-phenylpropyl, 4-butylphenyl, 3,5-dimethylphenyl, 3,5-bis(trifluoromethyl)-phenyl, 3,4-dimethoxyphenyl, 4'-ethyl-4-biphenyl, 3,4,5-trimethoxyphenyl, 3,4,5-triethoxyphenyl, propyl, hexyl, 2-propyl, 2-butyl, isobutyl, 2-methylbutyl, isovaleryl, 1-propenyl, 2-propenyl, 3-hepten-3-yl, p-tolyl, p-anisyl, t-butyl, cyclohexyl, cyclohexylmethyl, 3-cyclohexylpropyl, cycloheptyl, methyl, 2-methylcyclopropyl, cyclobutyl, cyclopentyl, 2-cyclopentylethyl, 2-furyl, 2-cyclohexylethyl, 4-methylcyclohexyl, 4-t-butylcyclohexyl, 4-methylcyclohexanemethyl, 2-buten-2-yl, 2-norboranemethyl, 1-adamantanemethyl, and 2-thienyl;
X is selected from the group consisting of a nitrogen atom and a sulfur atom; and
Y is selected from the group consisting of a hydrogen and methyl.

4. The library of claim 3, wherein R¹ is selected from the group consisting of a hydrogen atom, 9-fluoro, 8-fluoro, 8-bromo, 8-hydroxy, 11-methyl, 8-methyl, 9-methyl and 10-methyl.

5. The library of claim 1, wherein the compounds are bound to a solid-phase amino resin through the amide of the structure depicted, one hydrogen atom of the amide being absent.

6. A single imidazole compound comprising the structure:

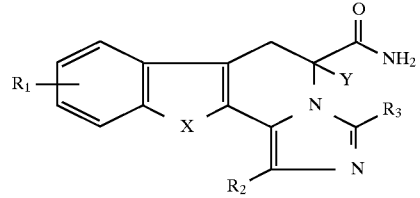

wherein:
R¹ is selected from the group consisting of a hydrogen atom, halo, hydroxy, protected hydroxy, $C_3$ to $C_{10}$ alkyl, $C_1$ to $C_{10}$ substituted alkyl, amino, carboxy, and protected carboxy;
R² is selected from the group consisting of a hydrogen atom, $C_1$ to $C_{10}$ alkyl, $C_3$ to $C_{10}$ substituted alkyl, phenyl, substituted phenyl, $C_7$ to $C_{16}$ phenylalkyl, $C_7$ to $C_{16}$ substituted phenylalkyl, $C_3$ to $C_7$ cycloalkyl, $C_3$ to $C_7$ substituted cycloalkyl, benzyl, substituted benzyl, naphthyl, substituted naphthyl, and when taken in conjunction with C1 and N2 to form a piperidine or benzopiperidine;
R³ is selected from the group consisting of $C_1$ to $C_{10}$ alkyl, $C_1$ to $C_{10}$ substituted alkyl, $C_2$ to $C_{10}$ alkenyl, $C_2$ to $C_{10}$ substituted alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, $C_7$ to $C_{16}$ phenylalkenyl, $C_7$ to $C_{16}$ substituted phenylalkenyl, benzyl, substituted benzyl, naphthyl, substituted naphthyl, heterocycle, and substituted heterocycle;
X is a nitrogen atom (N) or a sulfur atom (S); and
Y is selected from the group consisting of a hydrogen atom and methyl.

7. The compound of claim 6, wherein:
R¹ is selected from the group consisting of a hydrogen atom, halo, hydroxy, and $C_1$ to $C_{10}$ alkyl;
R² is selected from the group consisting of a hydrogen atom, $C_1$ to $C_{10}$ alkyl, $C_1$ to $C_{10}$ substituted alkyl, phenyl, $C_3$ to $C_7$ substituted cycloalkyl, benzyl, substituted benzyl, substituted naphthyl, and when taken in conjunction with C1 and N2 to form a piperidine or benzopiperidine;
R³ is selected from the group consisting of $C_1$ to $C_{10}$ alkyl, $C_1$ to $C_{10}$ substituted alkyl, $C_2$ to $C_{10}$ alkenyl, $C_3$ to $C_7$ cycloalkyl, $C_3$ to $C_7$ substituted cycloalkyl, phenyl, substituted phenyl, $C_7$ to $C_{16}$ phenylalkyl, $C_7$ to $C_{16}$ substituted phenylalkyl, $C_7$ to $C_{16}$ phenylalkenyl, $C_7$ to $C_{16}$ substituted phenylalkenyl, and heterocycle;
X is selected from the group consisting of a nitrogen atom and a sulfur atom; and
Y is selected from the group consisting of a hydrogen atom and methyl.

8. The compound of claim 6, wherein:

$R^1$ is selected from the group consisting of a hydrogen atom, fluoro, bromo, hydroxy, and methyl;

$R^2$ is selected from the group consisting of methyl, benzyl, a hydrogen atom, 3-imidazoylmethyl, aminobutyl, methylsulfinylethyl, carbamoylethyl, 4-hydroxybenzyl, ethyl, propyl, butyl, aminopropyl, phenyl, naphthylmethyl, cyclohexylmethyl, methylsulfonylethyl, 4-nitrobenzyl, 4-chlorobenzyl, 4-fluorobenzyl, 3-pyridylmethyl, 2-thienylmethyl, 1-butyl, 4-ethoxybenzyl, and when taken in conjunction with C1 and N2 to form a piperidine or benzopiperidine;

$R^3$ is selected from the group consisting of 1-phenylcyclopropyl, 1-phenylproply, 2-phenylpropyl, 3-methylbenzyl, 3-fluorobenzyl, 3-bromobenzyl, 3-trifluoromethylbenzyl, 4-methylbenzyl, 4-fluorobenzyl, 3-methoxybenzyl, 4-bromobenzyl, 4-methoxybenzyl, 4-ethoxybenzyl, 4-isobutylphenethyl, 3,4-dichlorobenzyl, 3,5-bis(trifluoromethyl)-benzyl, 3,4-dimethoxyphenethyl, 4-phenylbenzyl, α-methylstyryl, 2-trifluoromethylstyryl, 3,4-dimethoxybenzyl, 3,4-dihydroxybenzyl, 2-methoxystyryl, 3,4-dihydroxystyryl, 2-hydroxystyryl, phenyl, 4-chlorostyryl, m-anisyl, 4-isopropylphenyl, 4-vinylphenyl, 4-fluorophenyl, 4-bromophenyl, 3,4-dimethoxystyryl, 4-hydroxyphenyl, styryl, 3,4-dimethylphenyl, 3-fluoro-4-methylphenyl, 3-bromo-4-methylphenyl, 3-iodo-4-methylphenyl, 3,4-dichlorophenyl, 4-biphenyl, 3,4-difluorophenyl, m-tolyl, benzyl, phenethyl, 3-methoxy-4-methylphenyl, 3-phenylpropyl, 4-butylphenyl, 3,5-dimethylphenyl, 3,5-bis(trifluoromethyl)-phenyl, 3,4-dimethoxyphenyl, 4'-ethyl-4-biphenyl, 3,4,5-trimethoxyphenyl, 3,4,5-triethoxyphenyl, propyl, hexyl, 2-propyl, 2-butyl, isobutyl, 2-methylbutyl, isovaleryl, 1-propenyl, 2-propenyl, 3-hepten-3-yl, p-tolyl, p-anisyl, t-butyl, cyclohexyl, cyclohexylmethyl, 3-cyclohexylpropyl, cycloheptyl, methyl, 2-methylcyclopropyl, cyclobutyl, cyclopentyl, 2-cyclopentylethyl, 2-furyl, 2-cyclohexylethyl, 4-methylcyclohexyl, 4-t-butylcyclohexyl, 4-methylcyclohexanemethyl, 2-buten-2-yl, 2-norboranemethyl, 1-adamantanemethyl, and 2-thienyl;

X is selected from the group consisting of a nitrogen atom and a sulfur atom; and Y is selected from the group consisting of a hydrogen atom and methyl.

9. The compound of claim 8, wherein $R^1$ is selected from the group consisting of a hydrogen atom, 9-fluoro, 8-fluoro, 8-bromo, 8-hydroxy, 11-methyl, 8-methyl, 9-methyl and 10-methyl.

10. A method for the preparation of a library of claim 1, comprising condensing two or more resin-bound acylated dipeptides, wherein the C-terminal amino acid of the dipeptide is selected from the group consisting of a tryptophan derivative and a β-(3-benzothienyl) alanine derivative.

11. A method for the preparation of a library of claim 1, comprising the following steps:

(a) coupling an amino-protected first amino acid to a functionalized amine resin, said first amino acid selected from the group consisting of a tryptophan derivative and a β-(3-benzothienyl) alanine;

(b) deprotecting the first amino acid;

(c) coupling a protected second amino acid to obtain a resin-bound dipeptide;

(d) deprotecting the amino-terminus of the resin-bound dipeptide;

(e) acylating the resin-bound dipeptide with a carboxylic acid to obtain an acylated resin-bound dipeptide; and (f) condensing the acylated resin-bound dipeptide to form an imidazole compound, wherein steps (a) through (f) are performed on at least one mixture of two or more said first or second amino acids or said carboxylic acids to obtain a library of two or more imidazole compounds.

12. The method of claim 11, wherein the condensation step (f) is performed in the presence of a non-aromatic solvent with a reagent selected from the group consisting of phosphorous oxychloride, phosphorous chloride and phosphorous pentoxide.

13. The method of claim 11, further comprising deprotecting the side chains of said protected second amino acid after step (e) and before step (f).

14. The method of claim 11, further comprising cleaving the library from the resin.

* * * * *